(12) United States Patent
Skidmore

(10) Patent No.: US 8,499,252 B2
(45) Date of Patent: Jul. 30, 2013

(54) DISPLAY OF RESPIRATORY DATA GRAPHS ON A VENTILATOR GRAPHICAL USER INTERFACE

(75) Inventor: John Skidmore, San Diego, CA (US)

(73) Assignee: Covidien LP, Mansfield, MA (US)

( * ) Notice: Subject to any disclaimer, the term of this patent is extended or adjusted under 35 U.S.C. 154(b) by 300 days.

(21) Appl. No.: 12/844,579

(22) Filed: Jul. 27, 2010

(65) Prior Publication Data
US 2012/0030611 A1 Feb. 2, 2012

(51) Int. Cl.
*G06F 3/048* (2006.01)

(52) U.S. Cl.
USPC .......................................... 715/777; 715/781

(58) Field of Classification Search
USPC .......................................... 715/777, 781, 810
See application file for complete search history.

(56) References Cited

U.S. PATENT DOCUMENTS

| | | |
|---|---|---|
| 3,577,984 A | 5/1971 | Levy et al. |
| 3,659,590 A | 5/1972 | Jones et al. |
| 3,871,371 A | 3/1975 | Weigl |
| 3,940,742 A | 2/1976 | Hudspeth et al. |
| 3,961,624 A | 6/1976 | Weigl |
| 3,961,627 A | 6/1976 | Ernst et al. |
| 3,977,394 A | 8/1976 | Jones et al. |
| 3,991,304 A | 11/1976 | Hillsman |
| 3,996,928 A | 12/1976 | Marx |
| 4,034,743 A | 7/1977 | Greenwood et al. |
| 4,036,217 A | 7/1977 | Ito et al. |
| 4,053,951 A | 10/1977 | Hudspeth et al. |
| 4,090,513 A | 5/1978 | Togawa |
| 4,112,931 A | 9/1978 | Burns |
| 4,187,842 A | 2/1980 | Schreiber |
| 4,215,409 A | 7/1980 | Strowe |
| 4,241,739 A | 12/1980 | Elson |
| 4,258,718 A | 3/1981 | Goldman |
| 4,296,756 A | 10/1981 | Dunning et al. |
| 4,308,872 A | 1/1982 | Watson et al. |
| 4,323,064 A | 4/1982 | Hoenig et al. |

(Continued)

FOREIGN PATENT DOCUMENTS

| | | |
|---|---|---|
| EP | 0414777 | 3/1991 |
| EP | 1374938 | 1/2004 |

(Continued)

OTHER PUBLICATIONS

PCT International Search Report and Written Opinion in Application PCT/US2010/058131, mailed May 18, 2011, 12 pgs.

(Continued)

*Primary Examiner* — Omar Abdul-Ali

(57) ABSTRACT

The disclosure describes improved systems and methods for configuring the layout of a graphical display in a ventilatory system. Specifically, the present methods provide a user interface for configuring one or more layout categories associated with data on the graphical display. Upon selection of a layout category, a clinician is provided with a preview of the layout of the layout category. The preview consists of one or more parameter positions. Each parameter position is associated with a parameter. The clinician is also provided with a listing of possible parameters. The parameter positions in the preview and the possible parameters in the listing are selectable elements. Once a parameter position is selected, a possible parameter can be chosen to replace the parameter associated with the selected parameter position. If this replacement is acceptable to the clinician, the clinician can access an accept button to implement the replacement in the graphical display.

20 Claims, 7 Drawing Sheets

U.S. PATENT DOCUMENTS

| | | |
|---|---|---|
| 4,326,513 A | 4/1982 | Schulz et al. |
| 4,391,283 A | 7/1983 | Sharpless et al. |
| 4,401,115 A | 8/1983 | Monnier |
| 4,401,116 A | 8/1983 | Fry et al. |
| 4,407,295 A | 10/1983 | Steuer et al. |
| 4,440,177 A | 4/1984 | Anderson et al. |
| 4,444,201 A | 4/1984 | Itoh |
| 4,463,764 A | 8/1984 | Anderson et al. |
| 4,473,081 A | 9/1984 | Dioguardi et al. |
| 4,495,944 A | 1/1985 | Brisson et al. |
| 4,537,190 A | 8/1985 | Caillot et al. |
| 4,550,726 A | 11/1985 | McEwen |
| 4,579,115 A | 4/1986 | Wallroth et al. |
| 4,637,385 A | 1/1987 | Rusz |
| 4,654,029 A | 3/1987 | D'Antonio |
| 4,736,750 A | 4/1988 | Valdespino et al. |
| 4,752,089 A | 6/1988 | Carter |
| 4,790,327 A | 12/1988 | Despotis |
| 4,796,639 A | 1/1989 | Snow et al. |
| 4,813,409 A | 3/1989 | Ismach |
| 4,852,582 A | 8/1989 | Pell |
| 4,867,152 A | 9/1989 | Kou et al. |
| 4,876,903 A | 10/1989 | Budinger |
| 4,878,175 A | 10/1989 | Norden-Paul et al. |
| 4,917,108 A | 4/1990 | Mault |
| 4,921,642 A | 5/1990 | LaTorraca |
| 4,954,799 A | 9/1990 | Kumar |
| 4,984,158 A | 1/1991 | Hillsman |
| 4,990,894 A | 2/1991 | Loescher et al. |
| 5,003,985 A | 4/1991 | White et al. |
| 5,004,472 A | 4/1991 | Wallace |
| 5,009,662 A | 4/1991 | Wallace et al. |
| 5,020,527 A | 6/1991 | Dessertine |
| 5,021,046 A | 6/1991 | Wallace |
| 5,057,822 A | 10/1991 | Hoffman |
| 5,058,601 A | 10/1991 | Riker |
| 5,072,737 A | 12/1991 | Goulding |
| 5,137,026 A | 8/1992 | Waterson et al. |
| 5,150,291 A | 9/1992 | Cummings et al. |
| 5,161,525 A | 11/1992 | Kimm et al. |
| 5,163,423 A | 11/1992 | Suzuki |
| 5,167,506 A | 12/1992 | Kilis et al. |
| 5,203,343 A | 4/1993 | Axe et al. |
| 5,224,487 A | 7/1993 | Bellofatto et al. |
| 5,231,981 A | 8/1993 | Schreiber et al. |
| 5,235,973 A | 8/1993 | Levinson |
| 5,237,987 A | 8/1993 | Anderson et al. |
| 5,246,010 A | 9/1993 | Gazzara et al. |
| 5,251,632 A | 10/1993 | Delpy |
| 5,253,362 A | 10/1993 | Nolan et al. |
| 5,261,397 A | 11/1993 | Grunstein |
| 5,261,415 A | 11/1993 | Dussault |
| 5,271,389 A | 12/1993 | Isaza et al. |
| 5,277,195 A | 1/1994 | Williams |
| 5,279,304 A | 1/1994 | Einhorn et al. |
| 5,279,549 A | 1/1994 | Ranford |
| 5,293,875 A | 3/1994 | Stone |
| 5,299,568 A | 4/1994 | Forare et al. |
| 5,301,921 A | 4/1994 | Kumar |
| 5,303,698 A | 4/1994 | Tobia et al. |
| 5,303,699 A | 4/1994 | Bonassa et al. |
| 5,307,795 A | 5/1994 | Whitwam et al. |
| 5,319,355 A | 6/1994 | Russek |
| 5,319,540 A | 6/1994 | Isaza et al. |
| 5,325,861 A | 7/1994 | Goulding |
| 5,333,106 A | 7/1994 | Lanpher et al. |
| 5,333,606 A | 8/1994 | Schneider et al. |
| 5,339,807 A | 8/1994 | Carter |
| 5,339,825 A | 8/1994 | McNaughton et al. |
| 5,343,857 A | 9/1994 | Schneider et al. |
| 5,351,522 A | 10/1994 | Lura |
| 5,355,893 A | 10/1994 | Mick et al. |
| 5,357,946 A | 10/1994 | Kee et al. |
| 5,357,975 A | 10/1994 | Kraemer et al. |
| 5,363,842 A | 11/1994 | Mishelevich et al. |
| 5,365,922 A | 11/1994 | Raemer |
| 5,368,019 A | 11/1994 | LaTorraca |
| 5,373,851 A | 12/1994 | Reinhold, Jr. et al. |
| 5,383,449 A | 1/1995 | Forare et al. |
| 5,383,470 A | 1/1995 | Kolbly |
| 5,385,142 A | 1/1995 | Brady et al. |
| 5,390,666 A | 2/1995 | Kimm et al. |
| 5,401,135 A | 3/1995 | Stoen et al. |
| 5,402,796 A | 4/1995 | Packer et al. |
| 5,404,871 A | 4/1995 | Goodman et al. |
| 5,407,174 A | 4/1995 | Kumar |
| 5,413,110 A | 5/1995 | Cummings et al. |
| 5,438,980 A | 8/1995 | Phillips |
| 5,442,940 A | 8/1995 | Secker et al. |
| 5,443,075 A | 8/1995 | Holscher |
| 5,445,160 A | 8/1995 | Culver et al. |
| 5,446,449 A | 8/1995 | Lhomer et al. |
| 5,448,996 A | 9/1995 | Bellin et al. |
| 5,452,714 A | 9/1995 | Anderson et al. |
| 5,456,264 A | 10/1995 | Series et al. |
| 5,464,410 A | 11/1995 | Skeens et al. |
| 5,479,939 A | 1/1996 | Ogino |
| 5,487,731 A | 1/1996 | Denton |
| 5,495,848 A | 3/1996 | Aylsworth et al. |
| 5,501,231 A | 3/1996 | Kaish |
| 5,507,291 A | 4/1996 | Stirbl et al. |
| 5,513,631 A | 5/1996 | McWilliams |
| 5,517,983 A | 5/1996 | Deighan et al. |
| 5,517,985 A | 5/1996 | Kirk et al. |
| 5,518,002 A | 5/1996 | Wolf et al. |
| 5,520,071 A | 5/1996 | Jones |
| 5,524,615 A | 6/1996 | Power |
| 5,531,221 A | 7/1996 | Power |
| 5,534,851 A | 7/1996 | Russek |
| 5,537,992 A | 7/1996 | Bjoernstijerna et al. |
| 5,542,410 A | 8/1996 | Goodman et al. |
| 5,542,415 A | 8/1996 | Brody |
| 5,544,674 A | 8/1996 | Kelly |
| 5,548,702 A | 8/1996 | Li et al. |
| 5,549,106 A | 8/1996 | Gruenke et al. |
| 5,549,117 A | 8/1996 | Tacklind et al. |
| 5,553,620 A | 9/1996 | Snider et al. |
| 5,558,086 A | 9/1996 | Smith et al. |
| 5,560,353 A | 10/1996 | Willemot et al. |
| 5,564,414 A | 10/1996 | Walker et al. |
| 5,564,432 A | 10/1996 | Thomson |
| 5,571,142 A | 11/1996 | Brown et al. |
| 5,575,283 A | 11/1996 | Sjoestrand |
| 5,582,167 A | 12/1996 | Joseph |
| 5,590,648 A | 1/1997 | Mitchell et al. |
| 5,591,130 A | 1/1997 | Denton |
| 5,596,984 A | 1/1997 | O'Mahony et al. |
| 5,606,976 A | 3/1997 | Marshall et al. |
| 5,611,335 A | 3/1997 | Makhoul et al. |
| 5,626,144 A | 5/1997 | Tacklind et al. |
| 5,630,411 A | 5/1997 | Holscher |
| 5,632,270 A | 5/1997 | O'Mahony et al. |
| 5,632,281 A | 5/1997 | Rayburn |
| 5,634,461 A | 6/1997 | Faithfull et al. |
| 5,634,471 A | 6/1997 | Fairfax et al. |
| 5,642,735 A | 7/1997 | Kolbly |
| 5,645,048 A | 7/1997 | Brodsky et al. |
| 5,647,346 A | 7/1997 | Holscher |
| 5,651,264 A | 7/1997 | Lo et al. |
| 5,655,516 A | 8/1997 | Goodman et al. |
| 5,660,168 A | 8/1997 | Ottosson et al. |
| 5,660,171 A | 8/1997 | Kimm et al. |
| 5,664,560 A | 9/1997 | Merrick et al. |
| 5,664,562 A | 9/1997 | Bourdon |
| 5,669,379 A | 9/1997 | Somerson et al. |
| 5,671,767 A | 9/1997 | Kelly |
| 5,672,041 A | 9/1997 | Ringdahl et al. |
| 5,673,689 A | 10/1997 | Power |
| 5,676,129 A | 10/1997 | Rocci, Jr. et al. |
| 5,676,132 A | 10/1997 | Tillotson et al. |
| 5,678,539 A | 10/1997 | Schubert et al. |
| 5,683,424 A | 11/1997 | Brown et al. |
| 5,692,497 A | 12/1997 | Schnitzer et al. |
| 5,697,959 A | 12/1997 | Poore |
| 5,704,346 A | 1/1998 | Inoue |
| 5,704,366 A | 1/1998 | Tacklind et al. |
| 5,704,367 A | 1/1998 | Ishikawa et al. |

| | | | | | |
|---|---|---|---|---|---|
| 5,706,801 A | 1/1998 | Remes et al. | 6,135,106 A | 10/2000 | Dirks et al. |
| 5,715,812 A | 2/1998 | Deighan et al. | 6,142,150 A | 11/2000 | O'Mahoney et al. |
| 5,724,990 A | 3/1998 | Ogino | 6,148,814 A | 11/2000 | Clemmer et al. |
| 5,730,140 A | 3/1998 | Fitch | 6,148,815 A | 11/2000 | Wolf |
| 5,730,145 A | 3/1998 | Defares et al. | 6,155,257 A | 12/2000 | Lurie et al. |
| 5,735,287 A | 4/1998 | Thomson | 6,158,432 A | 12/2000 | Biondi et al. |
| 5,736,974 A | 4/1998 | Selker | 6,159,147 A | 12/2000 | Lichter et al. |
| 5,738,092 A | 4/1998 | Mock et al. | 6,161,539 A | 12/2000 | Winter |
| 5,740,792 A | 4/1998 | Ashley et al. | 6,162,183 A | 12/2000 | Hoover |
| 5,743,267 A | 4/1998 | Nikolic et al. | 6,167,362 A | 12/2000 | Brown et al. |
| 5,752,506 A | 5/1998 | Richardson | 6,168,568 B1 | 1/2001 | Gavriely |
| 5,752,509 A | 5/1998 | Lachmann et al. | 6,171,264 B1 | 1/2001 | Bader |
| 5,755,218 A | 5/1998 | Johansson et al. | 6,176,833 B1 | 1/2001 | Thomson |
| 5,758,652 A | 6/1998 | Nikolic | 6,186,956 B1 | 2/2001 | McNamee |
| 5,762,480 A | 6/1998 | Adahan | 6,190,326 B1 | 2/2001 | McKinnon et al. |
| 5,771,884 A | 6/1998 | Yarnall et al. | 6,192,876 B1 | 2/2001 | Denyer et al. |
| 5,778,874 A | 7/1998 | Maguire et al. | 6,198,963 B1 | 3/2001 | Haim et al. |
| 5,791,339 A | 8/1998 | Winter | 6,199,550 B1 | 3/2001 | Wiesmann et al. |
| 5,794,612 A | 8/1998 | Wachter et al. | 6,202,642 B1 | 3/2001 | McKinnon et al. |
| 5,794,986 A | 8/1998 | Gansel et al. | 6,213,955 B1 | 4/2001 | Karakasoglu et al. |
| 5,800,361 A | 9/1998 | Rayburn | 6,220,245 B1 | 4/2001 | Takabayashi et al. |
| 5,806,514 A | 9/1998 | Mock et al. | 6,223,744 B1 | 5/2001 | Garon |
| 5,809,997 A | 9/1998 | Wolf | 6,224,553 B1 | 5/2001 | Nevo |
| 5,813,397 A | 9/1998 | Goodman et al. | 6,233,539 B1 | 5/2001 | Brown |
| 5,813,399 A | 9/1998 | Isaza et al. | 6,234,963 B1 | 5/2001 | Blike et al. |
| 5,819,723 A | 10/1998 | Joseph | 6,240,920 B1 | 6/2001 | Strom |
| 5,822,715 A | 10/1998 | Worthington et al. | 6,251,082 B1 | 6/2001 | Rayburn |
| 5,826,570 A | 10/1998 | Goodman et al. | 6,261,238 B1 | 7/2001 | Gavriely |
| 5,826,575 A | 10/1998 | Lall | 6,262,728 B1 | 7/2001 | Alexander |
| 5,827,179 A | 10/1998 | Lichter et al. | 6,269,810 B1 | 8/2001 | Brooker et al. |
| 5,829,441 A | 11/1998 | Kidd et al. | 6,269,812 B1 | 8/2001 | Wallace et al. |
| 5,839,430 A | 11/1998 | Cama | 6,273,088 B1 | 8/2001 | Hillsman |
| 5,864,938 A | 2/1999 | Gansel et al. | 6,273,444 B1 | 8/2001 | Power |
| 5,865,168 A | 2/1999 | Isaza | 6,279,574 B1 | 8/2001 | Richardson et al. |
| 5,865,171 A | 2/1999 | Cinquin | 6,283,119 B1 | 9/2001 | Bourdon |
| 5,865,174 A | 2/1999 | Kloeppel | 6,283,923 B1 | 9/2001 | Finkelstein et al. |
| 5,875,777 A | 3/1999 | Eriksson | 6,287,264 B1 | 9/2001 | Hoffman |
| 5,878,744 A | 3/1999 | Pfeiffer | 6,301,497 B1 | 10/2001 | Neustadter |
| 5,881,717 A | 3/1999 | Isaza | 6,302,106 B1 | 10/2001 | Lewis |
| 5,881,723 A | 3/1999 | Wallace et al. | 6,305,373 B1 | 10/2001 | Wallace et al. |
| 5,884,622 A | 3/1999 | Younes | 6,321,748 B1 | 11/2001 | O'Mahoney |
| 5,884,623 A | 3/1999 | Winter | 6,322,502 B1 | 11/2001 | Schoenberg et al. |
| 5,891,023 A | 4/1999 | Lynn | 6,325,785 B1 | 12/2001 | Babkes et al. |
| 5,899,203 A | 5/1999 | Defares et al. | 6,339,410 B1 | 1/2002 | Milner et al. |
| 5,909,731 A | 6/1999 | O'Mahony et al. | 6,340,348 B1 | 1/2002 | Krishnan et al. |
| 5,915,379 A | 6/1999 | Wallace et al. | 6,342,040 B1 | 1/2002 | Starr et al. |
| 5,915,380 A | 6/1999 | Wallace et al. | 6,349,722 B1 | 2/2002 | Gradon et al. |
| 5,915,382 A | 6/1999 | Power | 6,349,724 B1 | 2/2002 | Burton et al. |
| 5,918,597 A | 7/1999 | Jones et al. | 6,355,002 B1 | 3/2002 | Faram et al. |
| 5,921,238 A | 7/1999 | Bourdon | 6,357,438 B1 | 3/2002 | Hansen |
| 5,921,920 A | 7/1999 | Marshall et al. | 6,360,745 B1 | 3/2002 | Wallace et al. |
| 5,924,418 A | 7/1999 | Lewis | 6,362,620 B1 | 3/2002 | Debbins et al. |
| 5,931,160 A | 8/1999 | Gilmore et al. | 6,367,475 B1 | 4/2002 | Kofoed et al. |
| 5,932,812 A | 8/1999 | Delsing | 6,369,838 B1 | 4/2002 | Wallace et al. |
| 5,934,274 A | 8/1999 | Merrick et al. | 6,370,419 B1 | 4/2002 | Lampotang et al. |
| 5,937,854 A | 8/1999 | Stenzler | 6,377,046 B1 | 4/2002 | Debbins et al. |
| 5,956,501 A | 9/1999 | Brown | 6,379,301 B1 | 4/2002 | Worthington et al. |
| 5,957,861 A | 9/1999 | Combs et al. | 6,390,088 B1 | 5/2002 | Nohl et al. |
| 5,971,937 A | 10/1999 | Ekstrom | 6,390,091 B1 | 5/2002 | Banner et al. |
| 5,975,081 A | 11/1999 | Hood et al. | 6,390,092 B1 | 5/2002 | Leenhoven |
| 5,979,440 A | 11/1999 | Honkonen et al. | 6,390,977 B1 | 5/2002 | Faithfull et al. |
| 5,980,466 A | 11/1999 | Thomson | 6,402,698 B1 | 6/2002 | Mault |
| 6,012,450 A | 1/2000 | Rubsamen | 6,408,043 B1 | 6/2002 | Hu et al. |
| 6,017,315 A | 1/2000 | Starr et al. | 6,412,483 B1 | 7/2002 | Jones et al. |
| 6,024,089 A | 2/2000 | Wallace et al. | 6,415,792 B1 | 7/2002 | Schoolman |
| 6,026,323 A | 2/2000 | Skladnev et al. | 6,416,471 B1 | 7/2002 | Kumar et al. |
| 6,032,119 A | 2/2000 | Brown et al. | 6,421,650 B1 | 7/2002 | Goetz et al. |
| 6,041,780 A | 3/2000 | Richard et al. | 6,427,687 B1 | 8/2002 | Kirk |
| 6,047,860 A | 4/2000 | Sanders | 6,435,175 B1 | 8/2002 | Stenzler |
| 6,055,506 A | 4/2000 | Frasca, Jr. | 6,436,053 B1 | 8/2002 | Knapp, II et al. |
| 6,073,110 A | 6/2000 | Rhodes et al. | 6,439,229 B1 | 8/2002 | Du et al. |
| 6,076,523 A | 6/2000 | Jones et al. | 6,450,164 B1 | 9/2002 | Banner et al. |
| 6,099,481 A | 8/2000 | Daniels et al. | 6,454,708 B1 | 9/2002 | Ferguson et al. |
| 6,106,481 A | 8/2000 | Cohen | 6,459,933 B1 | 10/2002 | Lurie et al. |
| 6,116,240 A | 9/2000 | Merrick et al. | 6,463,930 B2 | 10/2002 | Biondi et al. |
| 6,116,464 A | 9/2000 | Sanders | 6,467,478 B1 | 10/2002 | Merrick et al. |
| 6,118,847 A | 9/2000 | Hernandez-Guerra et al. | 6,471,658 B1 | 10/2002 | Daniels et al. |
| 6,119,684 A | 9/2000 | Nohl et al. | 6,488,029 B1 | 12/2002 | Hood et al. |
| 6,123,073 A | 9/2000 | Schlawin et al. | 6,488,629 B1 | 12/2002 | Saetre et al. |

| Patent | Type | Date | Inventor |
|---|---|---|---|
| RE37,970 | E | 1/2003 | Costello, Jr. |
| 6,511,426 | B1 | 1/2003 | Hossack et al. |
| 6,512,938 | B2 | 1/2003 | Claure et al. |
| 6,515,683 | B1 | 2/2003 | Wright |
| 6,517,497 | B2 | 2/2003 | Rymut et al. |
| 6,533,723 | B1 | 3/2003 | Lockery et al. |
| 6,533,730 | B2 | 3/2003 | Strom |
| 6,543,449 | B1 | 4/2003 | Woodring et al. |
| 6,543,701 | B1 | 4/2003 | Ho |
| 6,544,192 | B2 | 4/2003 | Starr et al. |
| 6,546,930 | B1 | 4/2003 | Emerson et al. |
| 6,547,728 | B1 | 4/2003 | Cornuejols |
| 6,553,991 | B1 | 4/2003 | Isaza |
| 6,553,992 | B1 | 4/2003 | Berthon-Jones et al. |
| 6,557,553 | B1 | 5/2003 | Borrello |
| 6,557,554 | B1 | 5/2003 | Sugiura |
| 6,566,875 | B1 | 5/2003 | Hasson et al. |
| 6,571,122 | B2 | 5/2003 | Schroeppel et al. |
| 6,571,795 | B2 | 6/2003 | Bourdon |
| 6,571,796 | B2 | 6/2003 | Banner et al. |
| 6,578,575 | B1 | 6/2003 | Jonson |
| 6,581,592 | B1 | 6/2003 | Bathe et al. |
| 6,584,973 | B1 | 7/2003 | Biondi et al. |
| 6,597,939 | B1 | 7/2003 | Lampotang et al. |
| 6,599,252 | B2 | 7/2003 | Starr |
| 6,603,494 | B1 | 8/2003 | Banks et al. |
| 6,606,993 | B1 | 8/2003 | Wiesmann et al. |
| 6,620,106 | B2 | 9/2003 | Mault |
| 6,621,917 | B1 | 9/2003 | Vilser |
| 6,622,726 | B1 | 9/2003 | Du |
| 6,629,934 | B2 | 10/2003 | Mault et al. |
| 6,630,176 | B2 | 10/2003 | Li et al. |
| 6,644,310 | B1 | 11/2003 | Delache et al. |
| 6,644,312 | B2 | 11/2003 | Berthon-Jones et al. |
| 6,645,158 | B2 | 11/2003 | Mault |
| 6,650,346 | B1 | 11/2003 | Jaeger et al. |
| 6,651,653 | B1 | 11/2003 | Honkonen et al. |
| 6,656,129 | B2 | 12/2003 | Niles et al. |
| 6,668,824 | B1 | 12/2003 | Isaza et al. |
| 6,668,829 | B2 | 12/2003 | Biondi et al. |
| 6,671,529 | B2 | 12/2003 | Claure et al. |
| 6,673,018 | B2 | 1/2004 | Friedman |
| 6,675,801 | B2 | 1/2004 | Wallace et al. |
| 6,679,258 | B1 | 1/2004 | Strom |
| 6,681,764 | B1 | 1/2004 | Honkonen et al. |
| 6,698,423 | B1 | 3/2004 | Honkonen et al. |
| 6,707,476 | B1 | 3/2004 | Hochstedler |
| 6,708,688 | B1 | 3/2004 | Rubin et al. |
| 6,709,405 | B2 | 3/2004 | Jonson |
| 6,712,762 | B1 | 3/2004 | Lichter et al. |
| 6,718,974 | B1 | 4/2004 | Moberg |
| 6,718,975 | B2 | 4/2004 | Blomberg |
| 6,725,077 | B1 | 4/2004 | Balloni et al. |
| 6,725,447 | B1 | 4/2004 | Gilman et al. |
| 6,725,860 | B2 | 4/2004 | Wallroth et al. |
| 6,733,449 | B1 | 5/2004 | Krishnamurthy et al. |
| 6,738,079 | B1 | 5/2004 | Kellerman et al. |
| 6,739,337 | B2 | 5/2004 | Isaza |
| 6,740,046 | B2 | 5/2004 | Knapp, II et al. |
| 6,743,172 | B1 | 6/2004 | Blike |
| 6,744,374 | B1 | 6/2004 | Kuenzner |
| 6,745,764 | B2 | 6/2004 | Hickle |
| 6,755,193 | B2 | 6/2004 | Berthon-Jones et al. |
| 6,755,787 | B2 | 6/2004 | Hossack et al. |
| 6,760,610 | B2 | 7/2004 | Tschupp et al. |
| 6,761,167 | B1 | 7/2004 | Nadjafizadeh et al. |
| 6,761,168 | B1 | 7/2004 | Nadjafizadeh et al. |
| 6,776,159 | B2 | 8/2004 | Pelerossi et al. |
| 6,782,888 | B1 | 8/2004 | Friberg et al. |
| 6,790,178 | B1 | 9/2004 | Mault et al. |
| 6,792,066 | B1 | 9/2004 | Harder et al. |
| 6,796,305 | B1 | 9/2004 | Banner et al. |
| 6,801,227 | B2 | 10/2004 | Bocionek et al. |
| 6,801,802 | B2 | 10/2004 | Sitzman et al. |
| 6,805,118 | B2 | 10/2004 | Brooker et al. |
| 6,807,965 | B1 | 10/2004 | Hickle |
| 6,814,074 | B1 | 11/2004 | Nadjafizadeh et al. |
| 6,820,614 | B2 | 11/2004 | Bonutti |
| 6,820,618 | B2 | 11/2004 | Banner et al. |
| 6,822,223 | B2 | 11/2004 | Davis |
| 6,824,520 | B2 | 11/2004 | Orr et al. |
| 6,828,910 | B2 | 12/2004 | VanRyzin et al. |
| 6,830,046 | B2 | 12/2004 | Blakley et al. |
| 6,834,647 | B2 | 12/2004 | Blair et al. |
| 6,837,242 | B2 | 1/2005 | Younes |
| 6,839,753 | B2 | 1/2005 | Biondi et al. |
| 6,845,773 | B2 | 1/2005 | Berthon-Jones et al. |
| 6,858,006 | B2 | 2/2005 | MacCarter et al. |
| 6,860,266 | B2 | 3/2005 | Blike |
| 6,866,040 | B1 | 3/2005 | Bourdon |
| 6,866,629 | B2 | 3/2005 | Bardy |
| 6,893,397 | B2 | 5/2005 | Bardy |
| 6,899,103 | B1 | 5/2005 | Hood et al. |
| 6,899,683 | B2 | 5/2005 | Mault et al. |
| 6,899,684 | B2 | 5/2005 | Mault et al. |
| 6,910,481 | B2 | 6/2005 | Kimmel et al. |
| 6,921,369 | B1 | 7/2005 | Gehrke et al. |
| 6,923,079 | B1 | 8/2005 | Snibbe |
| 6,931,269 | B2 | 8/2005 | Terry |
| 6,932,083 | B2 | 8/2005 | Jones et al. |
| 6,932,767 | B2 | 8/2005 | Landry et al. |
| 6,947,780 | B2 | 9/2005 | Scharf |
| 6,951,541 | B2 | 10/2005 | Desmarais |
| 6,954,702 | B2 | 10/2005 | Pierry et al. |
| 6,956,572 | B2 | 10/2005 | Zaleski |
| 6,960,854 | B2 | 11/2005 | Nadjafizadeh et al. |
| 6,970,919 | B1 | 11/2005 | Doi et al. |
| 6,976,958 | B2 | 12/2005 | Quy |
| 6,986,347 | B2 | 1/2006 | Hickle |
| 6,997,185 | B2 | 2/2006 | Han et al. |
| 6,997,880 | B2 | 2/2006 | Carlebach et al. |
| 7,006,862 | B2 | 2/2006 | Kaufman et al. |
| 7,008,380 | B1 | 3/2006 | Rees et al. |
| 7,017,574 | B2 | 3/2006 | Biondi et al. |
| 7,019,652 | B2 | 3/2006 | Richardson |
| 7,033,323 | B2 | 4/2006 | Botbol et al. |
| 7,036,504 | B2 | 5/2006 | Wallace et al. |
| 7,039,878 | B2 | 5/2006 | Auer et al. |
| 7,040,315 | B1 | 5/2006 | Strömberg |
| 7,040,318 | B2 | 5/2006 | Däscher et al. |
| 7,040,321 | B2 | 5/2006 | Göbel |
| 7,046,254 | B2 | 5/2006 | Brown et al. |
| 7,047,092 | B2 | 5/2006 | Wimsatt |
| 7,051,736 | B2 | 5/2006 | Banner et al. |
| 7,062,251 | B2 | 6/2006 | Birkett et al. |
| 7,066,173 | B2 | 6/2006 | Banner et al. |
| 7,077,125 | B2 | 7/2006 | Scheuch |
| 7,077,131 | B2 | 7/2006 | Hansen |
| 7,081,091 | B2 | 7/2006 | Merrett et al. |
| 7,081,095 | B2 | 7/2006 | Lynn et al. |
| RE39,225 | E | 8/2006 | Isaza et al. |
| 7,083,574 | B2 | 8/2006 | Kline |
| 7,089,927 | B2 | 8/2006 | John et al. |
| 7,089,937 | B2 | 8/2006 | Berthon-Jones et al. |
| 7,094,208 | B2 | 8/2006 | Williams et al. |
| 7,116,810 | B2 | 10/2006 | Miller et al. |
| 7,117,438 | B2 * | 10/2006 | Wallace et al. ............... 715/709 |
| 7,128,578 | B2 | 10/2006 | Lampotang et al. |
| 7,137,074 | B1 | 11/2006 | Newton et al. |
| 7,147,600 | B2 | 12/2006 | Bardy |
| 7,156,808 | B2 | 1/2007 | Quy |
| 7,162,296 | B2 | 1/2007 | Leonhardt et al. |
| 7,164,972 | B2 | 1/2007 | Imhof et al. |
| 7,165,221 | B2 * | 1/2007 | Monteleone et al. ......... 715/738 |
| 7,169,112 | B2 | 1/2007 | Caldwell |
| 7,172,557 | B1 | 2/2007 | Parker |
| 7,182,083 | B2 | 2/2007 | Yanof et al. |
| 7,187,790 | B2 | 3/2007 | Sabol et al. |
| 7,188,621 | B2 | 3/2007 | DeVries et al. |
| 7,201,734 | B2 | 4/2007 | Hickle |
| 7,203,353 | B2 | 4/2007 | Klotz et al. |
| 7,210,478 | B2 | 5/2007 | Banner et al. |
| 7,211,049 | B2 | 5/2007 | Bradley et al. |
| 7,219,666 | B2 | 5/2007 | Friberg et al. |
| 7,220,230 | B2 | 5/2007 | Roteliuk et al. |
| 7,222,054 | B2 | 5/2007 | Geva |
| 7,223,965 | B2 | 5/2007 | Davis |
| 7,228,323 | B2 | 6/2007 | Angerer et al. |

| | | |
|---|---|---|
| 7,241,269 B2 | 7/2007 | McCawley et al. |
| 7,246,618 B2 | 7/2007 | Habashi |
| 7,247,154 B2 | 7/2007 | Hickle |
| 7,252,640 B2 | 8/2007 | Ni et al. |
| 7,261,690 B2 | 8/2007 | Teller et al. |
| 7,264,730 B2 | 9/2007 | Connell et al. |
| 7,270,126 B2 | 9/2007 | Wallace et al. |
| 7,275,540 B2 | 10/2007 | Bolam et al. |
| 7,278,579 B2 | 10/2007 | Loffredo et al. |
| 7,282,032 B2 | 10/2007 | Miller |
| 7,285,090 B2 | 10/2007 | Stivoric et al. |
| 7,294,105 B1 | 11/2007 | Islam |
| 7,294,112 B1 | 11/2007 | Dunlop |
| 7,298,280 B2 | 11/2007 | Voege et al. |
| 7,300,418 B2 | 11/2007 | Zaleski |
| 7,303,680 B2 | 12/2007 | Connell et al. |
| 7,308,550 B2 | 12/2007 | Cornett |
| 7,310,551 B1 | 12/2007 | Koh et al. |
| 7,310,720 B2 | 12/2007 | Cornett |
| 7,311,665 B2 | 12/2007 | Hawthorne et al. |
| 7,314,451 B2 | 1/2008 | Halperin et al. |
| 7,316,231 B2 | 1/2008 | Hickle |
| 7,318,808 B2 | 1/2008 | Tarassenko et al. |
| 7,318,892 B2 | 1/2008 | Connell et al. |
| 7,321,802 B2 | 1/2008 | Wasner et al. |
| 7,322,352 B2 | 1/2008 | Minshull et al. |
| 7,322,937 B2 | 1/2008 | Blomberg et al. |
| 7,331,340 B2 | 2/2008 | Barney |
| 7,333,969 B2 | 2/2008 | Lee et al. |
| 7,334,578 B2 | 2/2008 | Biondi et al. |
| 7,343,916 B2 | 3/2008 | Biondo et al. |
| 7,343,917 B2 | 3/2008 | Jones |
| 7,347,200 B2 | 3/2008 | Jones et al. |
| 7,347,207 B2 | 3/2008 | Ahlmen et al. |
| 7,351,340 B2 | 4/2008 | Connell et al. |
| 7,362,341 B2 | 4/2008 | McGuire et al. |
| 7,367,337 B2 | 5/2008 | Berthon-Jones et al. |
| 7,367,955 B2 | 5/2008 | Zhang et al. |
| 7,369,757 B2 | 5/2008 | Farbarik |
| 7,370,650 B2 | 5/2008 | Nadjafizadeh et al. |
| 7,374,535 B2 | 5/2008 | Schoenberg et al. |
| 7,377,276 B2 | 5/2008 | Roy et al. |
| 7,380,210 B2 | 5/2008 | Lontka et al. |
| RE40,365 E | 6/2008 | Kirchgeorg et al. |
| 7,383,148 B2 | 6/2008 | Ahmed |
| 7,387,610 B2 | 6/2008 | Stahmann et al. |
| 7,413,546 B2 | 8/2008 | Agutter et al. |
| 7,422,562 B2 | 9/2008 | Hatib et al. |
| 7,425,201 B2 | 9/2008 | Euliano et al. |
| 7,428,902 B2 | 9/2008 | Du et al. |
| 7,435,220 B2 | 10/2008 | Ranucci |
| 7,438,072 B2 | 10/2008 | Izuchukwu |
| 7,438,073 B2 | 10/2008 | Delache et al. |
| 7,448,383 B2 | 11/2008 | Delache et al. |
| 7,452,333 B2 | 11/2008 | Roteliuk |
| 7,460,959 B2 | 12/2008 | Jafari |
| 7,464,339 B2 | 12/2008 | Keenan, Jr. et al. |
| 7,469,698 B1 | 12/2008 | Childers et al. |
| 7,487,773 B2 | 2/2009 | Li |
| 7,487,774 B2 | 2/2009 | Acker |
| 7,490,085 B2 | 2/2009 | Walker et al. |
| 7,496,400 B2 | 2/2009 | Hoskonen et al. |
| 7,500,481 B2 | 3/2009 | Delache et al. |
| 7,504,954 B2 | 3/2009 | Spaeder |
| 7,512,450 B2 | 3/2009 | Ahmed |
| 7,512,593 B2 | 3/2009 | Karklins et al. |
| 7,527,053 B2 | 5/2009 | DeVries et al. |
| 7,527,054 B2 | 5/2009 | Misholi |
| 7,530,353 B2 | 5/2009 | Choncholas et al. |
| RE40,806 E | 6/2009 | Gradon et al. |
| 7,543,582 B2 | 6/2009 | Lu et al. |
| 7,548,833 B2 | 6/2009 | Ahmed |
| 7,552,731 B2 | 6/2009 | Jorczak et al. |
| 7,556,036 B2 | 7/2009 | Bouillon et al. |
| 7,559,903 B2 | 7/2009 | Moussavi et al. |
| 7,562,657 B2 | 7/2009 | Blanch et al. |
| 7,565,905 B2 | 7/2009 | Hickle |
| 7,584,712 B2 | 9/2009 | Lu |
| 7,590,551 B2 | 9/2009 | Auer |
| 7,597,099 B2 | 10/2009 | Jones et al. |
| 7,603,170 B2 | 10/2009 | Hatlestad et al. |
| 7,603,631 B2 | 10/2009 | Bermudez et al. |
| 7,606,668 B2 | 10/2009 | Pierry et al. |
| 7,609,138 B2 | 10/2009 | Dietrich et al. |
| 7,610,915 B2 | 11/2009 | Dittmann |
| 7,618,378 B2 | 11/2009 | Bingham et al. |
| 7,625,345 B2 | 12/2009 | Quinn |
| 7,630,755 B2 | 12/2009 | Stahmann et al. |
| 7,650,181 B2 | 1/2010 | Freeman et al. |
| 7,652,571 B2 | 1/2010 | Parkulo et al. |
| 7,654,802 B2 | 2/2010 | Crawford, Jr. et al. |
| 7,654,966 B2 | 2/2010 | Westinskow et al. |
| 7,658,188 B2 | 2/2010 | Halpern et al. |
| 7,662,106 B2 | 2/2010 | Daniels et al. |
| 7,668,579 B2 | 2/2010 | Lynn |
| 7,669,598 B2 | 3/2010 | Rick et al. |
| 7,671,733 B2 | 3/2010 | McNeal et al. |
| 7,678,063 B2 | 3/2010 | Felmlee et al. |
| 7,682,312 B2 | 3/2010 | Lurie |
| 7,684,931 B2 | 3/2010 | Pierry et al. |
| 7,693,697 B2 | 4/2010 | Westenskow et al. |
| 7,694,677 B2 | 4/2010 | Tang |
| 7,698,156 B2 | 4/2010 | Martucci et al. |
| 7,708,015 B2 | 5/2010 | Seeger et al. |
| 7,717,112 B2 | 5/2010 | Sun et al. |
| 7,717,113 B2 | 5/2010 | Andrieux |
| D618,356 S | 6/2010 | Ross |
| 7,731,663 B2 | 6/2010 | Averina et al. |
| 7,736,132 B2 | 6/2010 | Bliss et al. |
| 7,740,013 B2 | 6/2010 | Ishizaki et al. |
| 7,753,049 B2 | 7/2010 | Jorczak et al. |
| 7,766,012 B2 | 8/2010 | Scheuch et al. |
| 7,771,364 B2 | 8/2010 | Arbel et al. |
| 7,772,965 B2 | 8/2010 | Farhan et al. |
| 7,778,709 B2 | 8/2010 | Gollasch et al. |
| 7,778,851 B2 | 8/2010 | Schoenberg et al. |
| 7,784,461 B2 | 8/2010 | Figueiredo et al. |
| 7,785,263 B2 | 8/2010 | Roteliuk et al. |
| 7,785,265 B2 | 8/2010 | Schätzl |
| 7,793,659 B2 | 9/2010 | Breen |
| 7,793,660 B2 | 9/2010 | Kimmel et al. |
| 7,810,497 B2 | 10/2010 | Pittman et al. |
| 7,814,906 B2 | 10/2010 | Moretti |
| 7,819,815 B2 | 10/2010 | Younes |
| 7,823,588 B2 | 11/2010 | Hansen |
| 7,831,450 B2 | 11/2010 | Schoenberg et al. |
| 7,832,394 B2 | 11/2010 | Schechter et al. |
| 7,836,882 B1 | 11/2010 | Rumph et al. |
| 7,837,629 B2 | 11/2010 | Bardy |
| 7,850,619 B2 | 12/2010 | Gavish et al. |
| 7,855,656 B2 | 12/2010 | Maschke |
| 7,855,716 B2 | 12/2010 | McCreary et al. |
| 7,859,401 B2 | 12/2010 | Falck et al. |
| 7,866,317 B2 | 1/2011 | Muellinger et al. |
| 7,871,394 B2 | 1/2011 | Halbert et al. |
| D632,796 S | 2/2011 | Ross et al. |
| D632,797 S | 2/2011 | Ross et al. |
| 7,881,780 B2 | 2/2011 | Flaherty |
| 7,883,480 B2 | 2/2011 | Dunlop |
| 7,885,828 B2 | 2/2011 | Glaser-Seidnitzer et al. |
| 7,886,231 B2 | 2/2011 | Hopermann et al. |
| 7,891,353 B2 | 2/2011 | Chalvignac |
| 7,891,354 B2 | 2/2011 | Farbarik |
| 7,893,560 B2 | 2/2011 | Carter |
| 7,895,527 B2 | 2/2011 | Zaleski et al. |
| 7,909,033 B2 | 3/2011 | Faram |
| 7,912,537 B2 | 3/2011 | Lee et al. |
| 7,927,286 B2 | 4/2011 | Ranucci |
| 7,931,601 B2 | 4/2011 | Ranucci |
| D638,852 S | 5/2011 | Skidmore et al. |
| 7,953,419 B2 | 5/2011 | Jost et al. |
| 7,956,719 B2 | 6/2011 | Anderson, Jr. et al. |
| 7,958,892 B2 | 6/2011 | Kwok et al. |
| 7,970,450 B2 | 6/2011 | Kroecker et al. |
| 7,984,714 B2 | 7/2011 | Hausmann et al. |
| D643,535 S | 8/2011 | Ross et al. |
| 7,990,251 B1 | 8/2011 | Ford, Jr. |
| 7,992,557 B2 | 8/2011 | Nadjafizadeh et al. |

| | | |
|---|---|---|
| 8,001,967 B2 | 8/2011 | Wallace et al. |
| D645,158 S | 9/2011 | Sanchez et al. |
| 8,021,310 B2 | 9/2011 | Sanborn et al. |
| D649,157 S | 11/2011 | Skidmore et al. |
| D653,749 S | 2/2012 | Winter et al. |
| 8,113,062 B2 | 2/2012 | Graboi et al. |
| D655,405 S | 3/2012 | Winter et al. |
| D655,809 S | 3/2012 | Winter et al. |
| 8,181,648 B2 | 5/2012 | Perine et al. |
| 8,210,173 B2 | 7/2012 | Vandine |
| 8,210,174 B2 | 7/2012 | Farbarik |
| 8,239,780 B2 * | 8/2012 | Manetta et al. ............... 715/764 |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 2001/0056358 A1 | 12/2001 | Dulong et al. |
| 2002/0026941 A1 | 3/2002 | Biondi et al. |
| 2002/0044059 A1 | 4/2002 | Reeder et al. |
| 2002/0077863 A1 | 6/2002 | Rutledge et al. |
| 2002/0091548 A1 | 7/2002 | Auer et al. |
| 2002/0171682 A1 | 11/2002 | Frank et al. |
| 2002/0177758 A1 | 11/2002 | Schoenberg et al. |
| 2003/0060723 A1 | 3/2003 | Joo et al. |
| 2003/0062045 A1 | 4/2003 | Woodring et al. |
| 2003/0106553 A1 | 6/2003 | Vanderveen |
| 2003/0130567 A1 | 7/2003 | Mault et al. |
| 2003/0130595 A1 | 7/2003 | Mault |
| 2003/0140928 A1 | 7/2003 | Bui et al. |
| 2003/0140929 A1 | 7/2003 | Wilkes et al. |
| 2003/0141368 A1 | 7/2003 | Pascual et al. |
| 2003/0141981 A1 | 7/2003 | Bui et al. |
| 2003/0142138 A1 | 7/2003 | Brown et al. |
| 2003/0144878 A1 | 7/2003 | Wilkes et al. |
| 2003/0144880 A1 | 7/2003 | Talachian et al. |
| 2003/0144881 A1 | 7/2003 | Talachian et al. |
| 2003/0144882 A1 | 7/2003 | Talachian et al. |
| 2003/0201697 A1 | 10/2003 | Richardson |
| 2003/0204414 A1 | 10/2003 | Wilkes et al. |
| 2003/0204416 A1 | 10/2003 | Radpay et al. |
| 2003/0204419 A1 | 10/2003 | Wilkes et al. |
| 2003/0204420 A1 | 10/2003 | Wilkes et al. |
| 2003/0208152 A1 | 11/2003 | Avrahami et al. |
| 2003/0208465 A1 | 11/2003 | Yurko et al. |
| 2003/0222548 A1 | 12/2003 | Richardson et al. |
| 2003/0230308 A1 | 12/2003 | Linden |
| 2004/0010425 A1 | 1/2004 | Wilkes et al. |
| 2004/0021693 A1 | 2/2004 | Monteleone |
| 2004/0034289 A1 | 2/2004 | Teller et al. |
| 2004/0059604 A1 | 3/2004 | Zaleski |
| 2004/0073453 A1 | 4/2004 | Nenov et al. |
| 2004/0078231 A1 | 4/2004 | Wilkes et al. |
| 2004/0121767 A1 | 6/2004 | Simpson et al. |
| 2004/0122294 A1 | 6/2004 | Hatlestad et al. |
| 2004/0150525 A1 | 8/2004 | Wilson et al. |
| 2004/0167465 A1 | 8/2004 | Mihai et al. |
| 2004/0167804 A1 | 8/2004 | Simpson et al. |
| 2004/0172222 A1 | 9/2004 | Simpson et al. |
| 2004/0172300 A1 | 9/2004 | Mihai et al. |
| 2004/0172301 A1 | 9/2004 | Mihai et al. |
| 2004/0172302 A1 | 9/2004 | Martucci et al. |
| 2004/0176667 A1 | 9/2004 | Mihai et al. |
| 2004/0224293 A1 | 11/2004 | Penning et al. |
| 2004/0236240 A1 | 11/2004 | Kraus et al. |
| 2004/0249673 A1 | 12/2004 | Smith |
| 2005/0016534 A1 | 1/2005 | Ost |
| 2005/0033198 A1 | 2/2005 | Kehyayan et al. |
| 2005/0039748 A1 | 2/2005 | Andrieux |
| 2005/0054910 A1 | 3/2005 | Tremblay et al. |
| 2005/0055242 A1 | 3/2005 | Bello et al. |
| 2005/0055244 A1 | 3/2005 | Mullan et al. |
| 2005/0065817 A1 | 3/2005 | Mihai et al. |
| 2005/0075542 A1 | 4/2005 | Goldreich |
| 2005/0075904 A1 | 4/2005 | Wager et al. |
| 2005/0085869 A1 | 4/2005 | Tehrani et al. |
| 2005/0104860 A1 | 5/2005 | McCreary |
| 2005/0108057 A1 | 5/2005 | Cohen et al. |
| 2005/0112013 A1 | 5/2005 | DeVries et al. |
| 2005/0112325 A1 | 5/2005 | Hickle |
| 2005/0124866 A1 | 6/2005 | Elaz et al. |
| 2005/0133027 A1 | 6/2005 | Elaz et al. |
| 2005/0137480 A1 | 6/2005 | Alt et al. |
| 2005/0139212 A1 | 6/2005 | Bourdon |
| 2005/0139213 A1 | 6/2005 | Blike |
| 2005/0143632 A1 | 6/2005 | Elaz et al. |
| 2005/0156933 A1 | 7/2005 | Lee et al. |
| 2005/0171876 A1 | 8/2005 | Golden |
| 2005/0177096 A1 | 8/2005 | Bollish et al. |
| 2005/0188083 A1 | 8/2005 | Biondi et al. |
| 2005/0192488 A1 | 9/2005 | Bryenton et al. |
| 2005/0204310 A1 | 9/2005 | De Zwart et al. |
| 2005/0215904 A1 | 9/2005 | Sumanaweera et al. |
| 2005/0217674 A1 | 10/2005 | Burton et al. |
| 2005/0251040 A1 | 11/2005 | Relkuntwar et al. |
| 2005/0288571 A1 | 12/2005 | Perkins et al. |
| 2006/0047202 A1 | 3/2006 | Elliott |
| 2006/0078867 A1 | 4/2006 | Penny |
| 2006/0080140 A1 | 4/2006 | Buttner et al. |
| 2006/0080343 A1 | 4/2006 | Carter et al. |
| 2006/0102171 A1 | 5/2006 | Gavish |
| 2006/0122474 A1 | 6/2006 | Teller et al. |
| 2006/0129055 A1 | 6/2006 | Orr et al. |
| 2006/0144396 A1 | 7/2006 | DeVries et al. |
| 2006/0149144 A1 | 7/2006 | Lynn et al. |
| 2006/0149589 A1 | 7/2006 | Wager |
| 2006/0150982 A1 | 7/2006 | Wood |
| 2006/0155183 A1 | 7/2006 | Kroecker |
| 2006/0155206 A1 | 7/2006 | Lynn |
| 2006/0155207 A1 | 7/2006 | Lynn et al. |
| 2006/0161071 A1 | 7/2006 | Lynn et al. |
| 2006/0173257 A1 | 8/2006 | Nagai et al. |
| 2006/0174884 A1 | 8/2006 | Habashi |
| 2006/0178911 A1 | 8/2006 | Syed et al. |
| 2006/0189880 A1 | 8/2006 | Lynn et al. |
| 2006/0189900 A1 | 8/2006 | Flaherty |
| 2006/0195041 A1 | 8/2006 | Lynn et al. |
| 2006/0196507 A1 | 9/2006 | Bradley |
| 2006/0200009 A1 | 9/2006 | Wekell et al. |
| 2006/0213518 A1 | 9/2006 | DeVries et al. |
| 2006/0229822 A1 | 10/2006 | Theobald et al. |
| 2006/0235324 A1 | 10/2006 | Lynn |
| 2006/0237015 A1 | 10/2006 | Berthon-Jones et al. |
| 2006/0249151 A1 | 11/2006 | Gambone |
| 2006/0249153 A1 | 11/2006 | DeVries et al. |
| 2006/0264762 A1 | 11/2006 | Starr |
| 2006/0278221 A1 | 12/2006 | Schermeier et al. |
| 2006/0278222 A1 | 12/2006 | Schermeier et al. |
| 2006/0293609 A1 | 12/2006 | Stahmann et al. |
| 2006/0294464 A1 | 12/2006 | Tokimoto et al. |
| 2007/0000490 A1 | 1/2007 | DeVries et al. |
| 2007/0000494 A1 | 1/2007 | Banner et al. |
| 2007/0016441 A1 | 1/2007 | Stroup |
| 2007/0017515 A1 | 1/2007 | Wallace et al. |
| 2007/0021673 A1 | 1/2007 | Arbel et al. |
| 2007/0028921 A1 | 2/2007 | Banner et al. |
| 2007/0038081 A1 | 2/2007 | Eck et al. |
| 2007/0060812 A1 | 3/2007 | Harel et al. |
| 2007/0062532 A1 | 3/2007 | Choncholas |
| 2007/0062533 A1 | 3/2007 | Choncholas et al. |
| 2007/0073181 A1 | 3/2007 | Pu et al. |
| 2007/0077200 A1 | 4/2007 | Baker |
| 2007/0113849 A1 | 5/2007 | Matthews et al. |
| 2007/0119453 A1 | 5/2007 | Lu et al. |
| 2007/0123758 A1 | 5/2007 | Miesel et al. |
| 2007/0123792 A1 | 5/2007 | Kline |
| 2007/0129647 A1 | 6/2007 | Lynn |
| 2007/0149860 A1 | 6/2007 | Lynn et al. |
| 2007/0156060 A1 | 7/2007 | Cervantes |
| 2007/0156456 A1 | 7/2007 | McGillin et al. |
| 2007/0157931 A1 | 7/2007 | Parker et al. |
| 2007/0163589 A1 | 7/2007 | DeVries et al. |
| 2007/0179357 A1 | 8/2007 | Bardy |
| 2007/0185390 A1 | 8/2007 | Perkins et al. |
| 2007/0191697 A1 | 8/2007 | Lynn et al. |
| 2007/0199566 A1 | 8/2007 | Be'eri |
| 2007/0208438 A1 | 9/2007 | El-Mankabady et al. |

| | | | | | | |
|---|---|---|---|---|---|---|
| 2007/0215155 A1 | 9/2007 | Marx et al. | | 2009/0065004 A1 | 3/2009 | Childers et al. |
| 2007/0225574 A1 | 9/2007 | Ueda | | 2009/0076342 A1 | 3/2009 | Amurthur et al. |
| 2007/0227537 A1 | 10/2007 | Bemister et al. | | 2009/0124917 A1 | 5/2009 | Hatlestad et al. |
| 2007/0229249 A1 | 10/2007 | McNeal | | 2009/0125333 A1 | 5/2009 | Heywood et al. |
| 2007/0241884 A1 | 10/2007 | Yamazaki et al. | | 2009/0126734 A1 | 5/2009 | Dunsmore et al. |
| 2007/0265510 A1 | 11/2007 | Bardy | | 2009/0131758 A1 | 5/2009 | Heywood et al. |
| 2007/0265877 A1 | 11/2007 | Rice et al. | | 2009/0133701 A1 | 5/2009 | Brain |
| 2007/0271122 A1 | 11/2007 | Zaleski | | 2009/0143694 A1 | 6/2009 | Krauss et al. |
| 2007/0272241 A1 | 11/2007 | Sanborn et al. | | 2009/0145438 A1 | 6/2009 | Brain |
| 2007/0272242 A1 | 11/2007 | Sanborn et al. | | 2009/0149200 A1 | 6/2009 | Jayasinghe et al. |
| 2007/0273216 A1 | 11/2007 | Farbarik | | 2009/0149723 A1 | 6/2009 | Krauss et al. |
| 2007/0276439 A1 | 11/2007 | Miesel et al. | | 2009/0149743 A1 | 6/2009 | Barron et al. |
| 2007/0284361 A1 | 12/2007 | Nadjafizadeh et al. | | 2009/0149927 A1 | 6/2009 | Kneuer et al. |
| 2007/0293741 A1 | 12/2007 | Bardy | | 2009/0150184 A1 | 6/2009 | Spahn |
| 2008/0000477 A1 | 1/2008 | Huster et al. | | 2009/0165795 A1 | 7/2009 | Nadjafizadeh et al. |
| 2008/0000479 A1 | 1/2008 | Elaz et al. | | 2009/0171167 A1 | 7/2009 | Baker, Jr. |
| 2008/0007396 A1 | 1/2008 | Parkulo | | 2009/0171176 A1 | 7/2009 | Andersohn |
| 2008/0022215 A1 | 1/2008 | Lee et al. | | 2009/0192421 A1 | 7/2009 | Huster et al. |
| 2008/0033661 A1 | 2/2008 | Syroid et al. | | 2009/0205661 A1 | 8/2009 | Stephenson et al. |
| 2008/0039735 A1 | 2/2008 | Hickerson | | 2009/0205663 A1 | 8/2009 | Vandine et al. |
| 2008/0041380 A1 | 2/2008 | Wallace et al. | | 2009/0209828 A1 | 8/2009 | Musin |
| 2008/0045844 A1 | 2/2008 | Arbel et al. | | 2009/0209849 A1 | 8/2009 | Rowe et al. |
| 2008/0047554 A1 | 2/2008 | Roy et al. | | 2009/0216145 A1 | 8/2009 | Skerl et al. |
| 2008/0053438 A1 | 3/2008 | DeVries et al. | | 2009/0221926 A1 | 9/2009 | Younes |
| 2008/0053441 A1 | 3/2008 | Gottlib et al. | | 2009/0240523 A1 | 9/2009 | Friedlander et al. |
| 2008/0064963 A1 | 3/2008 | Schwaibold et al. | | 2009/0241952 A1 | 10/2009 | Nicolazzi et al. |
| 2008/0065420 A1 | 3/2008 | Tirinato et al. | | 2009/0241953 A1 | 10/2009 | Vandine et al. |
| 2008/0066753 A1 | 3/2008 | Martin et al. | | 2009/0241956 A1 | 10/2009 | Baker, Jr. et al. |
| 2008/0072896 A1 | 3/2008 | Setzer et al. | | 2009/0241957 A1 | 10/2009 | Baker, Jr. |
| 2008/0072900 A1 | 3/2008 | Kenyon et al. | | 2009/0241958 A1 | 10/2009 | Baker, Jr. |
| 2008/0072901 A1 | 3/2008 | Habashi | | 2009/0241962 A1 | 10/2009 | Jafari et al. |
| 2008/0072902 A1 | 3/2008 | Setzer et al. | | 2009/0244003 A1 | 10/2009 | Bonnat |
| 2008/0076970 A1 | 3/2008 | Foulis et al. | | 2009/0247891 A1 | 10/2009 | Wood |
| 2008/0077033 A1 | 3/2008 | Figueiredo et al. | | 2009/0249247 A1 | 10/2009 | Tseng et al. |
| 2008/0077038 A1 | 3/2008 | McDonough et al. | | 2009/0250054 A1 | 10/2009 | Loncar et al. |
| 2008/0077436 A1 | 3/2008 | Muradia | | 2009/0301486 A1 | 12/2009 | Masic |
| 2008/0078390 A1 | 4/2008 | Milne et al. | | 2009/0301487 A1 | 12/2009 | Masic |
| 2008/0083644 A1 | 4/2008 | Janbakhsh et al. | | 2009/0301490 A1 | 12/2009 | Masic |
| 2008/0086691 A1 | 4/2008 | Hopermann et al. | | 2009/0301491 A1 | 12/2009 | Masic et al. |
| 2008/0091122 A1 | 4/2008 | Dunlop | | 2010/0004517 A1 | 1/2010 | Bryenton et al. |
| 2008/0092043 A1 | 4/2008 | Trethewey | | 2010/0011307 A1 | 1/2010 | Desfossez et al. |
| 2008/0092894 A1 | 4/2008 | Nicolazzi et al. | | 2010/0022904 A1 | 1/2010 | Centen |
| 2008/0097234 A1 | 4/2008 | Nicolazzi et al. | | 2010/0024820 A1 | 2/2010 | Bourdon |
| 2008/0103368 A1 | 5/2008 | Craine et al. | | 2010/0030092 A1 | 2/2010 | Kristensen et al. |
| 2008/0110460 A1 | 5/2008 | Elaz et al. | | 2010/0048985 A1 | 2/2010 | Henke et al. |
| 2008/0125873 A1 | 5/2008 | Payne et al. | | 2010/0048986 A1 | 2/2010 | Henke et al. |
| 2008/0154100 A1 | 6/2008 | Thalmeier et al. | | 2010/0049034 A1 | 2/2010 | Eck et al. |
| 2008/0161653 A1 | 7/2008 | Lin et al. | | 2010/0049264 A1 | 2/2010 | Henke et al. |
| 2008/0172249 A1 | 7/2008 | Glaser-Seidnitzer | | 2010/0049265 A1 | 2/2010 | Henke et al. |
| 2008/0178880 A1 | 7/2008 | Christopher et al. | | 2010/0051026 A1 | 3/2010 | Graboi |
| 2008/0178882 A1 | 7/2008 | Christopher et al. | | 2010/0051029 A1 | 3/2010 | Jafari et al. |
| 2008/0183057 A1 | 7/2008 | Taube | | 2010/0056852 A1 | 3/2010 | Henke et al. |
| 2008/0185009 A1 | 8/2008 | Choncholas | | 2010/0056853 A1 | 3/2010 | Henke et al. |
| 2008/0205427 A1 | 8/2008 | Jost | | 2010/0056855 A1 | 3/2010 | Henke et al. |
| 2008/0208012 A1 | 8/2008 | Ali | | 2010/0056929 A1 | 3/2010 | Stahmann et al. |
| 2008/0214947 A1 | 9/2008 | Hunt et al. | | 2010/0056941 A1 | 3/2010 | Henke et al. |
| 2008/0230057 A1 | 9/2008 | Sutherland | | 2010/0056942 A1 | 3/2010 | Henke et al. |
| 2008/0236582 A1 | 10/2008 | Tehrani | | 2010/0057148 A1 | 3/2010 | Henke et al. |
| 2008/0236585 A1 | 10/2008 | Parker et al. | | 2010/0059061 A1 | 3/2010 | Brain |
| 2008/0243016 A1 | 10/2008 | Liao et al. | | 2010/0063348 A1 | 3/2010 | Henke et al. |
| 2008/0251070 A1 | 10/2008 | Pinskiy et al. | | 2010/0063350 A1 | 3/2010 | Henke et al. |
| 2008/0255880 A1 | 10/2008 | Beller et al. | | 2010/0063365 A1 | 3/2010 | Pisani et al. |
| 2008/0258929 A1 | 10/2008 | Maschke | | 2010/0069761 A1 | 3/2010 | Karst et al. |
| 2008/0270912 A1 | 10/2008 | Booth | | 2010/0069774 A1 | 3/2010 | Bingham et al. |
| 2008/0281219 A1 | 11/2008 | Glickman et al. | | 2010/0071689 A1 | 3/2010 | Thiessen |
| 2008/0293025 A1 | 11/2008 | Zamierowsi | | 2010/0071692 A1 | 3/2010 | Porges |
| 2008/0295830 A1 | 12/2008 | Martonen et al. | | 2010/0071695 A1 | 3/2010 | Thiessen |
| 2008/0295839 A1 | 12/2008 | Habashi | | 2010/0071696 A1 | 3/2010 | Jafari |
| 2008/0306351 A1 | 12/2008 | Izumi | | 2010/0071697 A1 | 3/2010 | Jafari et al. |
| 2008/0308109 A1 | 12/2008 | Brain | | 2010/0072055 A1 | 3/2010 | Tanaka et al. |
| 2008/0312954 A1 | 12/2008 | Ullrich et al. | | 2010/0076278 A1 | 3/2010 | van der Zande et al. |
| 2008/0319513 A1 | 12/2008 | Pu et al. | | 2010/0078017 A1 | 4/2010 | Andrieux et al. |
| 2009/0005651 A1 | 1/2009 | Ward et al. | | 2010/0078026 A1 | 4/2010 | Andrieux et al. |
| 2009/0007909 A1 | 1/2009 | Carrico | | 2010/0081119 A1 | 4/2010 | Jafari et al. |
| 2009/0038921 A1 | 2/2009 | Kaps et al. | | 2010/0081890 A1 | 4/2010 | Li et al. |
| 2009/0054743 A1 | 2/2009 | Stewart | | 2010/0081955 A1 | 4/2010 | Wood, Jr. et al. |
| 2009/0055735 A1 | 2/2009 | Zaleski | | 2010/0083968 A1 | 4/2010 | Wondka et al. |
| 2009/0062725 A1 | 3/2009 | Goebel | | 2010/0095961 A1 | 4/2010 | Tornesel et al. |
| 2009/0063181 A1 | 3/2009 | Nho et al. | | 2010/0130873 A1 | 5/2010 | Yuen et al. |

| | | | | | | |
|---|---|---|---|---|---|---|
| 2010/0139660 A1 | 6/2010 | Adahan | | 2012/0136222 A1 | 5/2012 | Doyle et al. |
| 2010/0147303 A1 | 6/2010 | Jafari et al. | | 2012/0137249 A1 | 5/2012 | Milne et al. |
| 2010/0160839 A1 | 6/2010 | Freeman et al. | | 2012/0137250 A1 | 5/2012 | Milne et al. |
| 2010/0186744 A1 | 7/2010 | Andrieux | | | | |
| 2010/0218765 A1 | 9/2010 | Jafari et al. | | FOREIGN PATENT DOCUMENTS | | |
| 2010/0218766 A1 | 9/2010 | Milne | | EP | 1421966 | 5/2004 |
| 2010/0218767 A1 | 9/2010 | Jafari et al. | | EP | 1464357 | 10/2004 |
| 2010/0236555 A1 | 9/2010 | Jafari et al. | | GB | 2319967 | 6/1998 |
| 2010/0242961 A1 | 9/2010 | Mougel et al. | | WO | WO9014852 A1 | 12/1990 |
| 2010/0274100 A1 | 10/2010 | Behar et al. | | WO | WO9308534 A1 | 4/1993 |
| 2010/0282259 A1 | 11/2010 | Figueiredo et al. | | WO | WO9312823 A2 | 7/1993 |
| 2010/0288283 A1 | 11/2010 | Campbell et al. | | WO | WO9314696 A1 | 8/1993 |
| 2010/0298718 A1 | 11/2010 | Gilham et al. | | WO | WO9414374 A1 | 7/1994 |
| 2010/0300446 A1 | 12/2010 | Nicolazzi et al. | | WO | WO9508471 A1 | 3/1995 |
| 2010/0312132 A1 | 12/2010 | Wood et al. | | WO | WO9532480 A1 | 11/1995 |
| 2010/0317980 A1 | 12/2010 | Guglielmino | | WO | WO9624285 A1 | 8/1996 |
| 2011/0004489 A1 | 1/2011 | Schoenberg et al. | | WO | WO9720592 A1 | 6/1997 |
| 2011/0009746 A1 | 1/2011 | Tran et al. | | WO | WO9811840 A1 | 3/1998 |
| 2011/0011400 A1 | 1/2011 | Gentner et al. | | WO | WO9814116 A2 | 4/1998 |
| 2011/0015493 A1 | 1/2011 | Koschek | | WO | WO9829790 A2 | 7/1998 |
| 2011/0023878 A1 | 2/2011 | Thiessen | | WO | WO9833554 A1 | 8/1998 |
| 2011/0023879 A1 | 2/2011 | Vandine et al. | | WO | WO9840014 A1 | 9/1998 |
| 2011/0023880 A1 | 2/2011 | Thiessen | | WO | WO9841267 A1 | 9/1998 |
| 2011/0023881 A1 | 2/2011 | Thiessen | | WO | WO9841267 C1 | 9/1998 |
| 2011/0029910 A1 | 2/2011 | Thiessen | | WO | WO9841269 A1 | 9/1998 |
| 2011/0041849 A1 | 2/2011 | Chen et al. | | WO | WO9841270 A1 | 9/1998 |
| 2011/0041850 A1 | 2/2011 | Vandine et al. | | WO | WO9841271 A1 | 9/1998 |
| 2011/0054289 A1 | 3/2011 | Derchak et al. | | WO | WO9858219 A1 | 12/1998 |
| 2011/0055720 A1 | 3/2011 | Potter et al. | | WO | WO9903524 A1 | 1/1999 |
| 2011/0098638 A1 | 4/2011 | Chawla et al. | | WO | WO9952431 A1 | 10/1999 |
| 2011/0126151 A1 | 5/2011 | Bean et al. | | WO | WO9952437 A1 | 10/1999 |
| 2011/0126829 A1 | 6/2011 | Carter et al. | | WO | WO9959460 A2 | 11/1999 |
| 2011/0126832 A1 | 6/2011 | Winter et al. | | WO | WO9962403 A1 | 12/1999 |
| 2011/0126834 A1 | 6/2011 | Winter et al. | | WO | WO0018293 A1 | 4/2000 |
| 2011/0126835 A1 | 6/2011 | Winter et al. | | WO | WO0019886 A1 | 4/2000 |
| 2011/0126836 A1 | 6/2011 | Winter et al. | | WO | WO0062664 A1 | 10/2000 |
| 2011/0126837 A1 | 6/2011 | Winter et al. | | WO | WO0100264 A1 | 1/2001 |
| 2011/0128008 A1 | 6/2011 | Carter | | WO | WO0100265 A1 | 1/2001 |
| 2011/0132361 A1 | 6/2011 | Sanchez | | WO | WO0128416 A1 | 4/2001 |
| 2011/0132362 A1 | 6/2011 | Sanchez | | WO | WO0134022 A1 | 5/2001 |
| 2011/0132364 A1 | 6/2011 | Ogilvie et al. | | WO | WO0245566 A2 | 6/2002 |
| 2011/0132365 A1 | 6/2011 | Patel et al. | | WO | WO02082967 A2 | 10/2002 |
| 2011/0132366 A1 | 6/2011 | Ogilvie et al. | | WO | WO03015005 A2 | 2/2003 |
| 2011/0132367 A1 | 6/2011 | Patel | | WO | WO03024317 A2 | 3/2003 |
| 2011/0132368 A1 | 6/2011 | Sanchez et al. | | WO | WO03045493 A2 | 6/2003 |
| 2011/0132369 A1 | 6/2011 | Sanchez | | WO | WO03053503 A1 | 7/2003 |
| 2011/0132371 A1 | 6/2011 | Sanchez et al. | | WO | WO03060650 A2 | 7/2003 |
| 2011/0133936 A1 | 6/2011 | Sanchez et al. | | WO | WO03060651 A2 | 7/2003 |
| 2011/0138308 A1 | 6/2011 | Palmer et al. | | WO | WO03075989 A2 | 9/2003 |
| 2011/0138309 A1 | 6/2011 | Skidmore et al. | | WO | WO03075990 A2 | 9/2003 |
| 2011/0138311 A1 | 6/2011 | Palmer | | WO | WO03075991 A1 | 9/2003 |
| 2011/0138315 A1 | 6/2011 | Vandine et al. | | WO | WO03084405 A2 | 10/2003 |
| 2011/0138323 A1 | 6/2011 | Skidmore et al. | | WO | WO2004014216 A2 | 2/2004 |
| 2011/0146681 A1 | 6/2011 | Jafari et al. | | WO | WO2004014226 A1 | 2/2004 |
| 2011/0146683 A1 | 6/2011 | Jafari et al. | | WO | WO2004032719 A2 | 4/2004 |
| 2011/0154241 A1 | 6/2011 | Skidmore et al. | | WO | WO2004043254 A1 | 5/2004 |
| 2011/0175728 A1 | 7/2011 | Baker, Jr. | | WO | WO2005010796 | 2/2005 |
| 2011/0196251 A1 | 8/2011 | Jourdain et al. | | WO | WO2005024729 A1 | 3/2005 |
| 2011/0209702 A1 | 9/2011 | Vuong et al. | | WO | WO2005055825 A1 | 6/2005 |
| 2011/0209704 A1 | 9/2011 | Jafari et al. | | WO | WO2005056087 A1 | 6/2005 |
| 2011/0209707 A1 | 9/2011 | Terhark | | WO | WO2005069740 A2 | 8/2005 |
| 2011/0213215 A1 | 9/2011 | Doyle et al. | | WO | WO2005077260 A1 | 8/2005 |
| 2011/0259330 A1 | 10/2011 | Jafari et al. | | WO | WO2005112739 A1 | 12/2005 |
| 2011/0259332 A1 | 10/2011 | Sanchez et al. | | WO | WO2006008745 A2 | 1/2006 |
| 2011/0259333 A1 | 10/2011 | Sanchez et al. | | WO | WO2006009830 A2 | 1/2006 |
| 2011/0265024 A1 | 10/2011 | Leone et al. | | WO | WO2006037184 A1 | 4/2006 |
| 2011/0271960 A1 | 11/2011 | Milne et al. | | WO | WO2006050388 A2 | 5/2006 |
| 2011/0273299 A1 | 11/2011 | Milne et al. | | WO | WO2006051466 A1 | 5/2006 |
| 2012/0000467 A1 | 1/2012 | Milne et al. | | WO | WO2006078432 A2 | 7/2006 |
| 2012/0000468 A1 | 1/2012 | Milne et al. | | WO | WO2006094055 A2 | 9/2006 |
| 2012/0000469 A1 | 1/2012 | Milne et al. | | WO | WO2006096080 A1 | 9/2006 |
| 2012/0000470 A1 | 1/2012 | Milne et al. | | WO | WO2006109072 A2 | 10/2006 |
| 2012/0029317 A1 | 2/2012 | Doyle et al. | | WO | WO2006123956 A1 | 11/2006 |
| 2012/0060841 A1 | 3/2012 | Crawford, Jr. et al. | | WO | WO2006125986 A1 | 11/2006 |
| 2012/0066609 A1 | 3/2012 | Howard et al. | | WO | WO2006125987 A1 | 11/2006 |
| 2012/0071729 A1 | 3/2012 | Doyle et al. | | WO | WO2006125989 A1 | 11/2006 |
| 2012/0090611 A1 | 4/2012 | Graboi et al. | | WO | WO2006125990 A1 | 11/2006 |
| 2012/0096381 A1 | 4/2012 | Milne et al. | | WO | WO2006137067 A2 | 12/2006 |
| 2012/0133519 A1 | 5/2012 | Milne et al. | | WO | WO2007033050 A2 | 3/2007 |

| | | | |
|---|---|---|---|
| WO | WO2007106804 A2 | 9/2007 |
| WO | WO 2007145948 | 12/2007 |
| WO | WO2008030091 A1 | 3/2008 |
| WO | WO2008042699 A2 | 4/2008 |
| WO | WO2008058997 A2 | 5/2008 |
| WO | WO2008062554 A1 | 5/2008 |
| WO | WO2008113410 A1 | 9/2008 |
| WO | WO2008118951 A1 | 10/2008 |
| WO | WO2008140528 A1 | 11/2008 |
| WO | WO2008146264 A2 | 12/2008 |
| WO | WO2008148134 A1 | 12/2008 |
| WO | WO2009024967 A2 | 2/2009 |
| WO | WO2009027864 A1 | 3/2009 |
| WO | WO2009036334 A1 | 3/2009 |
| WO | WO2009124297 A1 | 10/2009 |
| WO | WO2010009531 A1 | 1/2010 |
| WO | WO2010020980 A1 | 2/2010 |
| WO | WO2010021730 A1 | 2/2010 |
| WO | WO2010039989 A1 | 4/2010 |
| WO | WO2010126916 A1 | 11/2010 |
| WO | WO2010141415 A1 | 12/2010 |
| WO | WO2011005953 A2 | 1/2011 |
| WO | WO2011022242 A1 | 2/2011 |

OTHER PUBLICATIONS

PCT International Search Report and Written Opinion in Application PCT/US2010/058132, mailed Mar. 3, 2011, 10 pgs.
U.S. Appl. No. 12/631,685, Office Action mailed Nov. 15, 2011, 22 pgs.
U.S. Appl. No. 12/631,685, Office Action mailed Feb. 29, 2012, 23 pgs.
U.S. Appl. No. 12/631,712, Office Action mailed Nov. 14, 2011, 20 pgs.
U.S. Appl. No. 12/631,712, Office Action mailed Feb. 29, 2012, 22 pgs.
U.S. Appl. No. 12/631,750, Office Action mailed Dec. 8, 2011, 12 pgs.
U.S. Appl. No. 12/631,752, Office Action mailed Dec. 8, 2011, 12 pgs.
U.S. Appl. No. 12/760,649, Office Action mailed Jan. 6, 2012, 11 pgs.
U.S. Appl. No. 12/631,685, Advisory Action mailed May 11, 2012, 3 pgs.
U.S. Appl. No. 12/631,712, Advisory Action mailed May 11, 2012, 3 pgs.
U.S. Appl. No. 12/631,750, Advisory Action mailed Jul. 24, 2012, 3 pgs.
U.S. Appl. No. 12/631,750, Office Action mailed May 16, 2012, 13 pgs.
U.S. Appl. No. 12/631,752, Notice of Allowance mailed Jun. 11, 2012, 8 pgs.
U.S. Appl. No. 12/631,752, Notice of Allowance mailed Jul. 24, 2012, 8 pgs.
U.S. Appl. No. 12/631,752, Office Action mailed Mar. 15, 2012, 13 pgs.
U.S. Appl. No. 12/760,649, Office Action mailed Jul. 20, 2012, 13 pgs.
US 7,284,551, 10/2007, Jones et al. (withdrawn).
7200 Series Ventilator, Options, and Accessories: Operator's Manual. Nellcor Puritan Bennett, Part No. 22300 A, Sep. 1990, pp. 1-196.
7200 Ventilatory System: Addendum/Errata. Nellcor Puritan Bennett, Part No. 4-023576-00, Rev. A, Apr. 1988, pp. 1-32.
800 Operator's and Technical Reference Manual. Series Ventilator System, Nellcor Puritan Bennett, Part No. 4-070088-00, Rev. L, Aug. 2010, pp. 1-476.
840 Operator's and Technical Reference Manual. Ventilator System, Nellcor Puritan Bennett, Part No. 4-075609-00, Rev. G, Oct. 2006, pp. 1-424.
PCT International Search Report mailed Apr. 7, 2011, Applicant's Reference H-RM-01984WO, International Application No. PCT/US2010/060871, International Filing Date Dec. 16, 2010, Applicant Nellcor Puritan Bennett LLC, 3 pgs.
U.S. Appl. No. 12/970,696, Office Action mailed Aug. 2, 2012, 12 pgs.
U.S. Appl. No. 12/631,750, Office Action mailed Oct. 4, 2012, 13 pgs.
U.S. Appl. No. 12/760,649, Advisory Action mailed Sep. 28, 2012, 3 pgs.
U.S. Appl. No. 12/970,696, Notice of Allowance mailed Jan. 15, 2013, 14 pgs.
U.S. Appl. No. 12/631,750, Office Action mailed Mar. 25, 2013, 15 pgs.

* cited by examiner

_US 8,499,252 B2_

DISPLAY OF RESPIRATORY DATA GRAPHS ON A VENTILATOR GRAPHICAL USER INTERFACE

RELATED APPLICATIONS

This application claims benefit under 35 U.S.C. §119(e) to U.S. Provisional Application No. 61/287,914, entitled "GRAPHICAL USER INTERFACE FOR USE ON MEDICAL VENTILATOR," filed on Dec. 18, 2009, the entire disclosure of which is hereby incorporated herein by reference.

INTRODUCTION

A ventilator is a device that mechanically helps patients breathe by replacing some or all of the muscular effort required to inflate and deflate the lungs. A ventilator may be configured with various settings and parameters for proper delivery of respiratory support. Indeed, many of the settings and/or parameters typically must be configured and input by a clinician prior to ventilation. In fact, in many cases, clinicians may be required to repeatedly enter the same settings and parameters manually for each new patient because they are based on uniform protocols or other specifications.

DISPLAY OF RESPIRATORY DATA GRAPHS ON A VENTILATOR GRAPHICAL USER INTERFACE

The disclosure describes improved systems and methods for configuring the layout of a graphical display in a ventilatory system. Specifically, the present methods provide a user interface for configuring one or more layout categories associated with data on the graphical display. For instance, each layout category can be represented as a selection element in a layout configuration window. Upon selection of a layout category, a clinician is provided with a preview of the layout of the layout category. The preview consists of one or more parameter positions. Each parameter position is associated with a parameter. The clinician is also provided with a listing of possible parameters. The parameter positions in the preview and the possible parameters in the listing are selectable elements. Once a parameter position is selected, a possible parameter can be chosen to replace the parameter associated with the selected parameter position. If this replacement is acceptable to the clinician, the clinician can access an accept button to implement the replacement in the graphical display.

Embodiments of the present disclosure may recite ventilator user interfaces for configuring the layout of a graphical display in a ventilatory system. Specifically, a ventilator may be configured with a computer having a user interface including a graphical user interface for accepting commands and for displaying information. The user interface may comprise at least one window associated with the user interface and one or more elements within the at least one window. The one or more elements may further comprise a first set of selection elements for selecting a layout category, a second set of selection elements for indicating a parameter position, and a third set of selection elements for indicating a replacement parameter for the parameter position. The first set of selection elements may further comprise a tab for selecting a patient data layout category, a tab for selecting a big numbers layout category, and a tab for selecting a charts layout category. The second set of selection elements may include a preview of the currently displayed parameter on the graphical display for each parameter position. The third set of selection elements may further comprise a listing of possible parameters for selection of the replacement parameter.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The following drawing figures, which from a part of this application, are illustrative of described technology and are not meant to limit the scope of the invention as claimed in any manner, which scope shall be based on the claims appended hereto.

DETAILED DESCRIPTION

Although the techniques introduced above and discussed in detail below may be implemented for a variety of medical devices, the present disclosure will discuss the implementation of these techniques for use in a mechanical ventilator system. The reader will understand that the technology described in the context of a ventilator system could be adapted for use with other therapeutic equipment having user interfaces, including graphical user interfaces (GUIs), for prompt startup of a therapeutic treatment.

This disclosure describes systems and methods for configuring the layout of a graphical display in a ventilatory system. Specifically, embodiments may provide a user interface, including a graphical user interface or other display interface, for configuring the layout of the graphical display. A layout configuration window may provide one or more layout categories for configuration. For instance, the ventilator may provide a clinician with an input element for selecting a layout category describing "Patient Data". Upon selecting the "Patient Data" layout category, a preview of the "Patient Data" parameters that are visible on the graphical display may appear in the layout configuration window. Below the preview, a listing of possible parameters that may replace the parameters in the preview are presented. In one embodiment, the listing is only visible once a parameter has been selected from the preview. Thereafter, when the clinician selects a replacement "Patient Data" parameter for a given position in the "Patient Data" parameter preview, a preview of the "Patient Data" parameters including the replacement "Patient Data" parameter is generated. If the layout configuration is acceptable to the clinician, the clinician may implement the preview as the configuration of the underlying graphical representation.

Alternatively, the layout configuration window may provide a clinician with an input element for selecting layout categories describing "Big Numbers" and "Charts". Again, the clinician may utilize the preview and listing of possible parameters to generate a new layout configuration for "Big Numbers" and/or "Charts". Additional input elements may also be provided within the spirit of the present invention.

As such, the present disclosure provides an institution or clinician with optimal control over routine ventilatory settings. Specifically, routine layout configuration settings may be preconfigured according to a hospital-specific, clinic-specific, physician-specific, or any other appropriate protocol. Moreover, layout configuration settings may be changed and edited in response to a particular patient's changing needs and/or condition.

Figure 1:
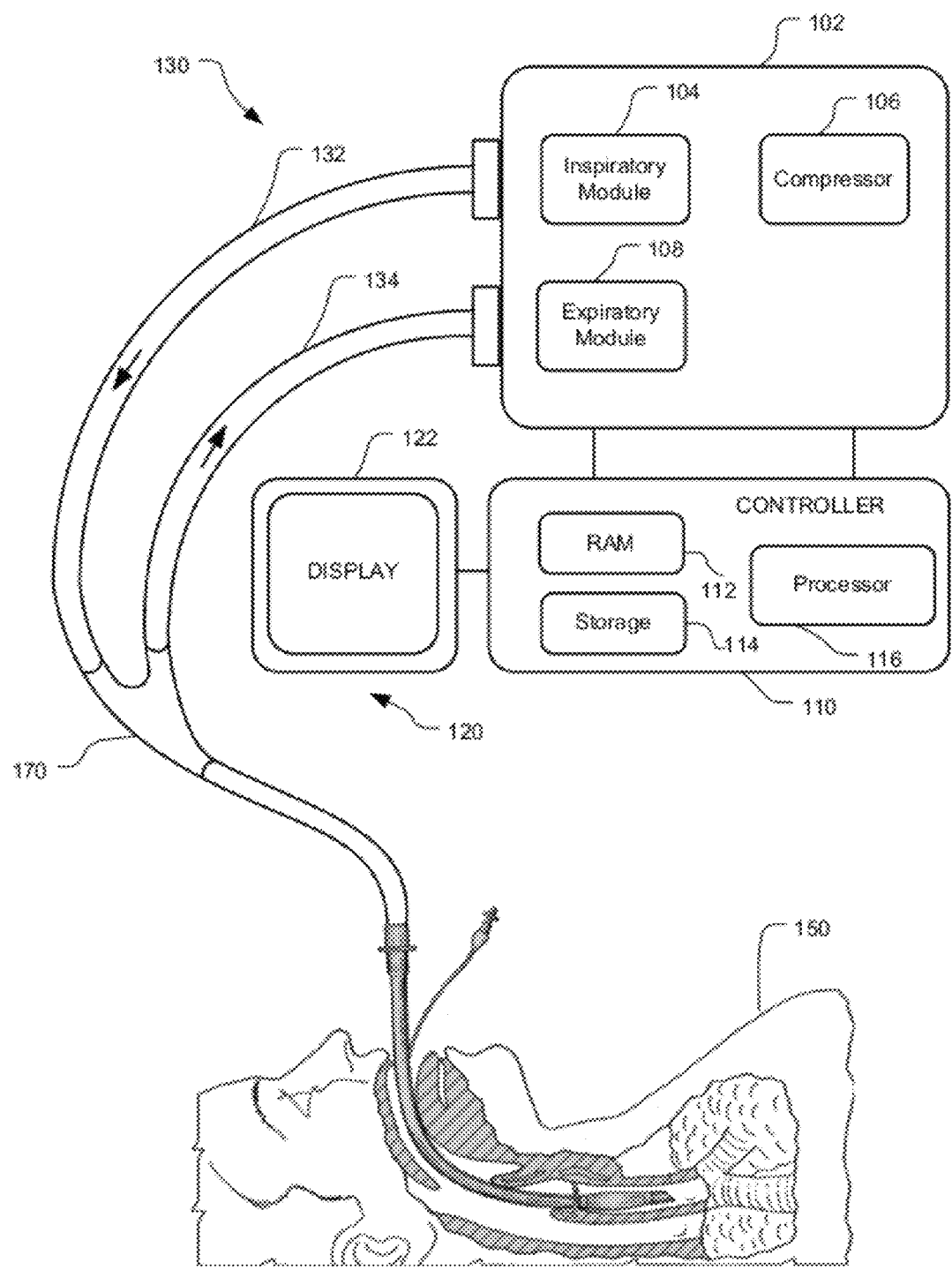
FIG. 1 is a diagram illustrating an embodiment of an exemplary ventilator connected to a human patient.

FIG. 1 illustrates an embodiment of a ventilator connected to a human patient 150. The ventilator includes a pneumatic system 102 (also referred to as a pressure generating system 102) for circulating breathing gases to and from patient 150 via the ventilation tubing system 130, which couples the patient to the pneumatic system via an invasive patient interface (e.g., endotracheal tube).

Ventilation tubing system 130 may be a two-limb (shown) or a one-limb circuit for carrying gas to and from the patient 150. In a two-limb embodiment as shown, a fitting, typically referred to as a "wye-fitting" 170, may be provided to couple the patient interface to an inspiratory limb 132 and an expiratory limb 134 of the ventilation tubing system 130.

Pneumatic system 102 may be configured in a variety of ways. In the present example, system 102 includes an expiratory module 108 coupled with the expiratory limb 134 and an inspiratory module 104 coupled with the inspiratory limb 132. Compressor 106 or other source(s) of pressurized gases (e.g., air, oxygen, and/or helium) is coupled with inspiratory module 104 to provide a gas source for ventilatory support via inspiratory limb 132.

The pneumatic system may include a variety of other components, including sources for pressurized air and/or oxygen, mixing modules, valves, sensors, tubing, accumulators, filters, etc. Controller 110 is operatively coupled with pneumatic system 102, signal measurement and acquisition systems, and an operator interface 120 that may enable an operator to interact with the ventilator (e.g., reset alarms, change ventilator settings, select operational modes, view monitored parameters, etc.). Controller 110 may include memory 112, one or more processors 116, storage 114, and/or other components of the type commonly found in command and control computing devices.

The memory 112 is computer-readable storage media that stores software that is executed by the processor 116 and which controls the operation of the ventilator. In an embodiment, the memory 112 includes one or more solid-state storage devices such as flash memory chips. In an alternative embodiment, the memory 112 may be mass storage connected to the processor 116 through a mass storage controller (not shown) and a communications bus (not shown).

Although the description of computer-readable media contained herein refers to a solid-state storage, it should be appreciated by those skilled in the art that computer-readable storage media can be any available media that can be accessed by the processor 116. Computer-readable storage media includes volatile and non-volatile, removable and non-removable media implemented in any method or technology for storage of information such as computer-readable instructions, data structures, program modules or other data. Computer-readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

As described in more detail below, controller 110 may monitor pneumatic system 102 in order to evaluate the condition of the patient and to ensure proper functioning of the ventilator based on various parameter settings. The specific parameter settings may be based on preconfigured settings applied to the controller 110, or based on input received via operator interface 120 and/or other components of the ventilator. In the depicted example, operator interface 120 includes a display 122 that is touch-sensitive, enabling the display to serve both as an input and output device.

Figure 2:
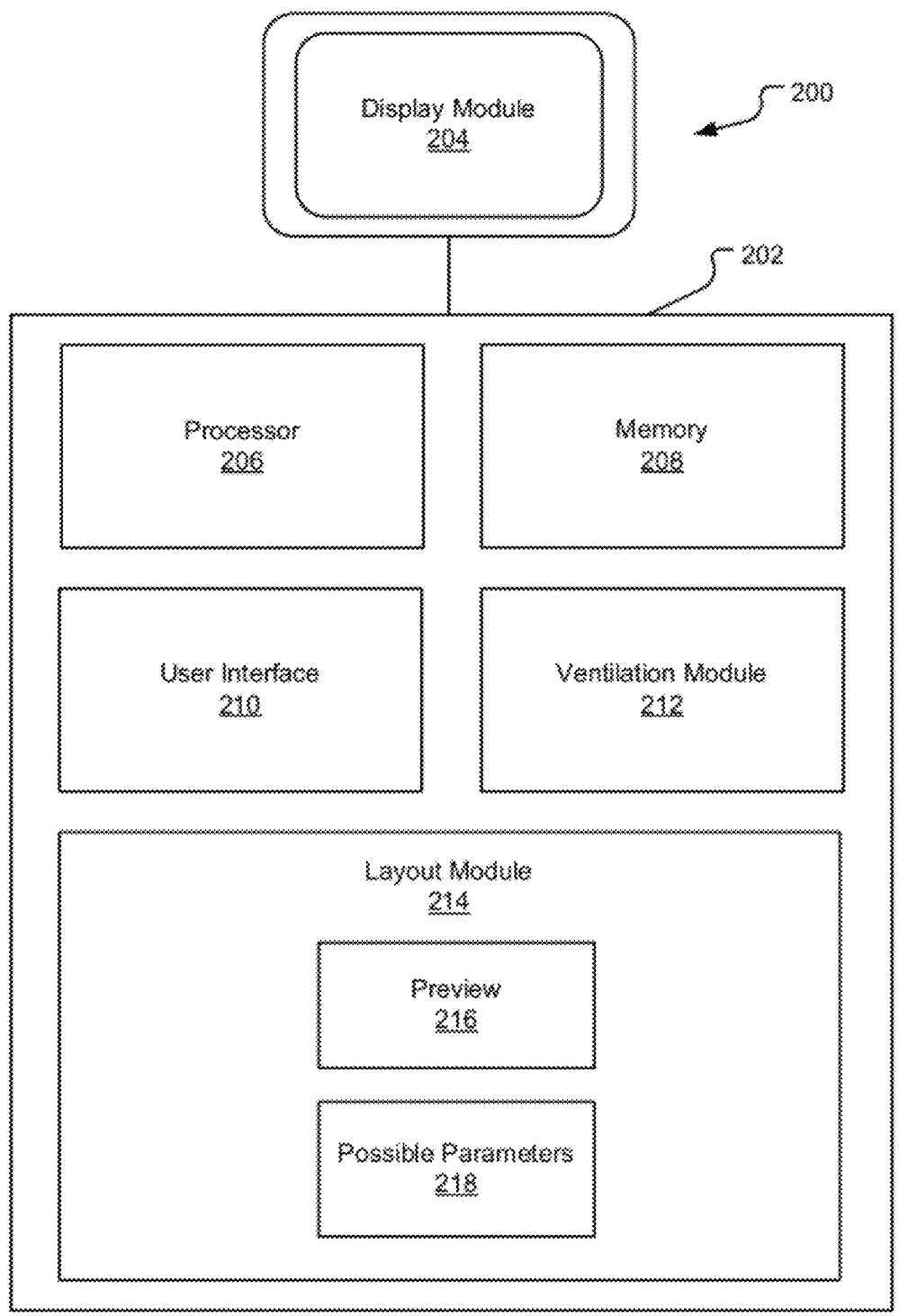
FIG. 2 is a block-diagram illustrating an embodiment of a ventilatory system having a user interface for configuring layout of the graphical display.

FIG. 2 is a block-diagram illustrating an embodiment of a ventilatory system having a user interface for efficiently and uniformly configuring layout of the graphical display.

The ventilator 202 includes a display module 204, memory 208, one or more processors 206, user interface 210, and ventilation module 212. Memory 208 is defined as described above for memory 112. Similarly, the one or more processors 206 are defined as described above for the one or more processors 116.

Ventilation module 212 may oversee ventilation according to appropriate parameter settings preconfigured according to any suitable protocol or specification. Alternatively, ventilation module 212 may oversee ventilation for a patient according to custom ventilatory settings, as determined appropriate by a clinician or institution and as manually input via user interface 210, or otherwise. For example, ventilation module 212 may monitor and regulate pressure delivery by any suitable method, either currently known or disclosed in the future, according to pressure parameter settings. Specifically, ventilation module 212 may be in communication with pneumatic system 102, including inspiratory module 104 coupled with inspiratory limb 132, and with compressor 106 or other source(s) of pressurized gases (e.g., air, oxygen, and/or helium). Compressor 106 may be coupled with inspiratory module 104, to provide a gas source for delivering air pressure via inspiratory limb 132. Ventilation module 212 may also be in communication with the layout module 214 to configure layout settings for the ventilatory parameters.

The display module 204 presents various input screens and displays to a clinician, including but not limited to one or more layout configuration screens, as will be described further herein, for configuring the layout of the display. The display module 204 is further configured to communicate with user interface 210. The display module 204 may provide a graphical user interface (GUI), providing various windows and elements to the clinician for input and interface command operations. User interface 210 may accept commands and input through display module 204 and may provide setup options to the clinician through a GUI on display module 204. Display module 204 may further be an interactive display, whereby the clinician may both receive and communicate information to the ventilator 202, as by a touch-activated user interface. Alternatively, user interface 210 may provide other suitable means of communication with the ventilator 202, for instance by a keyboard or other suitable interactive device.

The layout configuration options provided to the clinician through the user interface may include, among others, options for configuring the graphical display. Specifically, the user interface may allow a clinician to manually configure the layout for various layout categories encompassing one or more ventilatory parameters for presentation on the graphical display. Alternatively, the layout configuration settings can be initially established to reflect protocol-specific parameter layout settings. As such, layout module 214 may accept input values from a clinician for configuring the various layout modules 216-218. Layout module 214 may further be in communication with ventilation module 212. For instance, layout module 214 may communicate parameter configuration settings to ventilation module 212 such that the ventilator may properly monitor and regulate various parameters associated with the respiration of a patient. As noted above, layout module 214 may receive manual settings as input from user interface 210, e.g., via a graphical user interface.

Layout module 214 may also include layout modules 216-218. Layout modules 216-218 may each be associated with a particular layout category. Such layout categories may include, but are not limited to, "Patient Data", "Big Numbers", and "Charts". Layout Modules 216-218 are provided for exemplary purposes only and any number of useful layout modules representing any number of interesting and useful layout categories may be provided.

Figure 3:
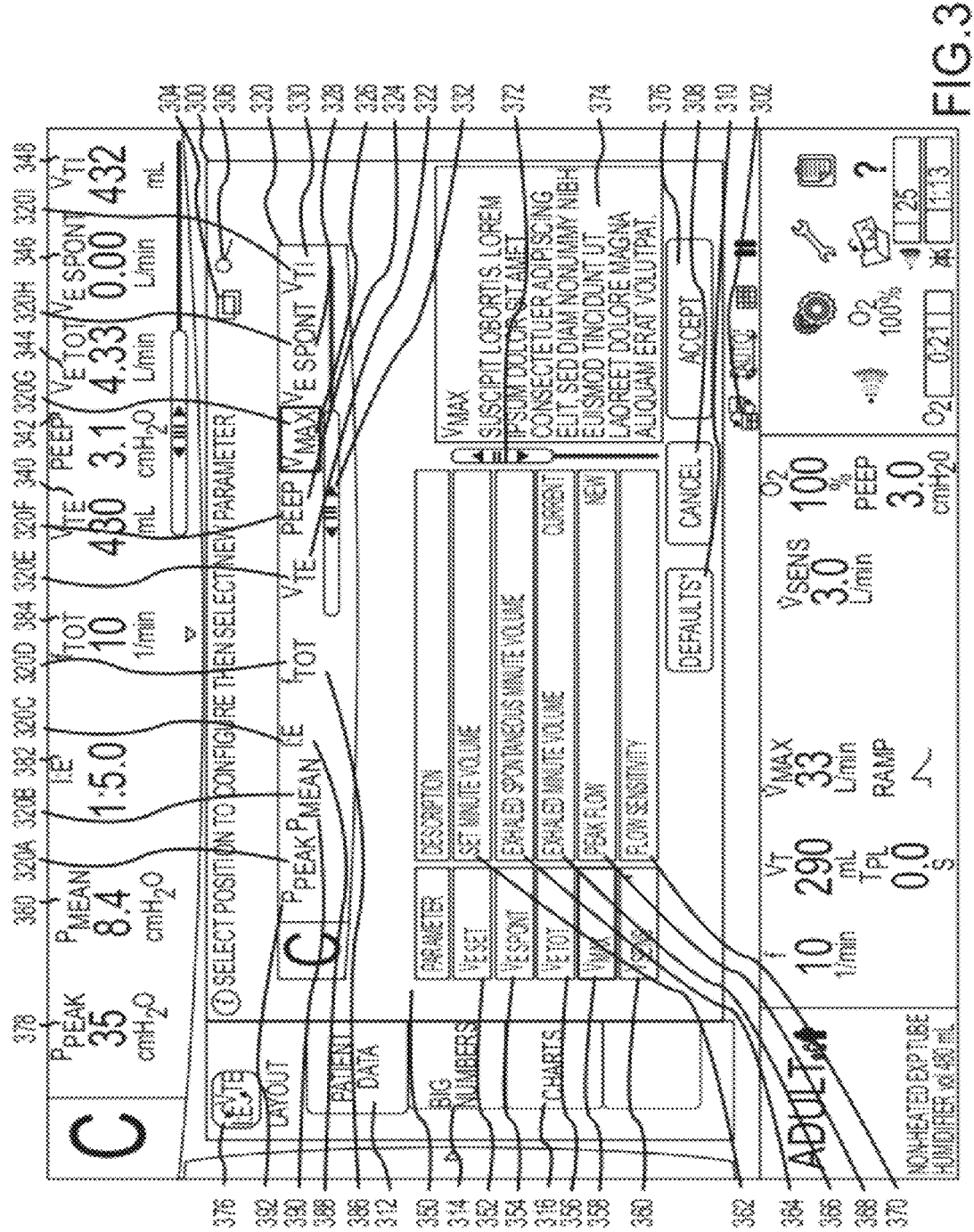
FIG. 3 is an illustration of an embodiment of a user interface for configuring layout settings for a "Patient Data" parameter.

Layout module 214 may include a preview module 216 for generating a preview of current parameter selections for the layout category. For example, as can be seen in FIG. 3, the current parameters for the "Patient Data" layout category are "$V_{TE}$" 322, "PEEP" 324, "$V_{MAX}$" 326, "$V_{ESPONT}$" 328, and "$V_{TI}$" 330. The "$V_{MAX}$" parameter 326 is included in this preview because it has been selected as a replacement parameter, as will be described below. If no replacements parameters have been selected, the preview module 216 will generate a preview that includes the parameters currently visible in the graphical display, as in FIG. 6.

Layout module 214 may also include a possible parameters module 218 for generating a listing 350 of possible parameters to replace the current parameters in a given layout category. For example, as can be seen in FIG. 3, the listing 350 of possible parameters includes "$V_{E\ SET}$", "$V_{E\ SPONT}$", "$V_{E\ TOT}$", "$V_{MAX}$", and "$V_{SENS}$" 352-360. The possible parameter module 218 also generates a concise description 362-370 to accompany each possible parameter 352-360. For example, in FIG. 3, the "$V_{MAX}$" 358 parameter is accompanied by a concise description of "Peak flow" 368. Included in this concise description 368 is an indication of whether the possible parameter is a parameter currently visible in the graphical display or if the possible parameter is a new parameter to the graphical display. In FIG. 3, the currently displayed "$V_{E\ TOT}$" parameter 356 includes the word "current" in its concise description 366. In addition, the selected "$V_{MAX}$" parameter 358 includes the word "new" in its concise description 368 as the "$V_{MAX}$" parameter 358 has been selected for that parameter position. The selection is indicated by a bold border. As will be appreciated by one skilled in the art, any method of indicating selection can be utilized, including but not limited to, changing the background color, changing the border, changing the font, or any other method known in the art. If a new parameter has not been selected, then the current parameter will be indicated as selected (not depicted).

For the selected parameter, the possible parameter module 218 also generates a detailed description box 374 of the selected parameter. As can be seen in FIG. 3, the "$V_{MAX}$" parameter 358 is selected. The detailed description box 374, therefore, includes a detailed description of the selected "$V_{MAX}$" parameter 358.

FIG. 3 is an illustration of an embodiment of a user interface 300 for modifying layout configuration settings for the graphical display.

Layout user interface may be accessed via any suitable means, for example via a main ventilatory user interface on display module. As illustrated, layout configuration user interface may provide one or more windows for display and one or more elements for selection and/or input. Windows may include one or more elements and, additionally, may provide graphical displays, instructions, or other useful information to the clinician. Elements may be displayed as buttons, tabs, icons, toggles, or any other suitable visual access element, etc., including any suitable element for input selection or control.

According to one embodiment, as illustrated in FIG. 3, layout configuration interface may include layout configuration window 300. Layout configuration window 300 includes a switch button 302 depicted in the upper left hand corner of the layout configuration window 300. When the switch button 302 is accessed, the layout configuration window 300 switches to the graphical display 700 illustrated in FIG. 7.

Layout configuration window 300 also includes a transparency button 304 and a pin-up button 306. When the transparency button 304 is accessed, the layout configuration window 300 may be viewed simultaneously with other data displayed on the graphical display 700, or other user interface. When the pin-up button 306 is accessed, the layout configuration window 300 may remain open unless and until a clinician desires to close the layout configuration window 300 by accessing the "Accept" button 376. Otherwise, the window 300 may close automatically after some period of inactivity. When the layout configuration window 300 is pinned, the changes will be implemented, but the layout configuration window 300 will not be closed.

Layout configuration window 300 also includes a "Defaults*" button 308. When the "Defaults*" button 308 is accessed, the layout configuration settings are reset to ventilator factory settings or institutional settings, if institutional settings are available.

Layout configuration window 300 also includes a cancel button 310. When a clinician decides not to modify the layout configuration settings for the graphical display, the clinician may select the cancel button 310 to exit the layout configuration window 300.

Layout configuration window 300 may also include a visual indication button 376. Visual indication button 376 visually indicates the function of the layout configuration window 300.

Layout configuration window 300 displays tabs 312-316 on the left hand side. The tabs 312-316 represent different layout categories. As can be appreciated by one skilled in the art, any number of tabs can be utilized on the layout configuration window 300. In the present embodiment, three tabs are displayed. The three tabs represent the following layout categories: "Patient Data" 312, "Big Numbers" 314, and "Charts" 316. A clinician can display layout information associated with a layout category by selecting the appropriate layout category tab on the layout configuration window 300. The layout configuration window 300 depicts an embodiment in which the "Patient Data" tab 312 has been selected for display.

When the "Patient Data" tab 312 is selected, as depicted in layout configuration window 300, the current "Patient Data" parameters 322-330 and 386-392 are displayed on preview toolbar 320. The "Patient Data" parameters 322-330 and 386-392 in the layout configuration window 300 correspond to the "Patient Data" parameters 340-348 and 378-384, respectively, displayed in the upper right hand corner of the underlying graphical display 700. The "Patient Data" parameters 340-348 and 378-384 in the underlying graphical display 700 correspond to real-time measurements of the patient. For example, the "$V_{ETOT}$" parameter 344 reflects the exhaled minute volume of the patient.

Unlike the "Patient Data" parameters 340-348 and 378-384 in the underlying graphical display 700, the "Patient Data" parameters 322-330 and 386-392 in the layout configuration window 300 do not include actual patient data. In the depicted embodiment, the preview toolbar 320 shows nine current "Patient Data" parameters 322-330 and 386-392, each "Patient Data" parameter 322-330 and 386-392 occupying one position of the nine allotted "Patient Data" parameter positions 320A-320I. As will be appreciated, the preview toolbar 320 can have any number of allotted "Patient Data" parameter positions 320A-320I. In one embodiment, there is a scrollbar 332 below the preview toolbar 320. When the scrollbar 332 is slid to the right one position, each displayed "Patient Data" parameter 322-330 and 386-392 is displaced one position to the left, the left most "Patient Data" parameter disappears from view, and a new "Patient Data" parameter fills the right most position. The scrollbar 332 can be moved to the right until a final "Patient Data" parameter fills the right most "Patient Data" parameter position. The scrollbar 332, therefore, allows a clinician to monitor various "Patient Data" parameters without occupying excessive space on the GUI.

In the depicted embodiment, the current "Patient Data" parameter positions in the underlying graphic display are occupied by "$P_{Peak}$" 378, "$P_{Mean}$" 380, "I:E" 382, "$f_{TOT}$" 384, "$V_{TE}$" 340, "PEEP" 342, "$V_{E\,TOT}$" 344, "$V_{ESPONT}$" 346 and "$V_{TI}$" 348. The layout configuration window, however, displays a preview toolbar 320 with "Patient Data" parameter positions occupied by "$P_{Peak}$" 392, "$P_{Mean}$" 390, "I:E" 388, "$f_{TOT}$" 386, "$V_{TE}$" 322, "PEEP" 324, "$V_{MAX}$" 324, "$V_{ESPONT}$" 326, and "$V_{TI}$" 328. The "$V_{MAX}$" parameter 326 is the replacement "Patient Data" parameter. The replacement "Patient Data" parameter will be described in detail below.

Below the preview toolbar 320 (and the scrollbar 332) is a listing 350 of possible "Patient Data" parameters 352-360, each possible "Patient Data" parameter 352-360 accompanied by a concise description 362-370. As can be appreciated by one skilled in the art, any number of possible "Patient Data" parameters can be included in the listing 350. In the exemplary layout configuration window 300, five possible "Patient Data" parameters are displayed: "$V_{E\,SET}$" 352, "$V_{E\,SPONT}$" 354, "$V_{E\,TOT}$" 356, "$V_{MAX}$" 358, and "$V_{SENS}$" 360. Additional "Patient Data" parameters can be displayed by accessing the scrollbar 372 to the right of listing 350. As depicted, each possible "Patient Data" 352-360 parameter is accompanied by a concise description 362-370. For example, the "$V_{MAX}$" parameter 358 is accompanied by a concise description of "Peak flow" 366. In one embodiment, the listing 350 is not displayed until a "Patient Data" parameter 322-330 and 386-392 is selected.

The listing 350 also indicates which possible "Patient Data" parameter is currently occupying a selected "Patient Data" parameter position. For example, the seventh "Patient Data" parameter position 320G on the toolbar 320 is currently selected. The selection is indicated by a bold border. As will be appreciated by one skilled in the art, any method of indicating selection can be utilized, including but limited to, changing the background color, changing the border, changing the font, or any other method known in the art. In the exemplary layout configuration window 300, the "$V_{E\,TOT}$" parameter 344 is currently occupying the seventh "Patient Data" parameter position. This occupation can be seen in the "Patient Data" parameters of the underlying graphical display. When a possible "Patient Data" parameter currently occupies the selected "Patient Data" parameter position of the underlying display, the concise description of the possible "Patient Data" parameter includes the word "current." For example, the concise description 366 of the "$V_{E\,TOT}$" parameter 352 in the listing 350 includes the word "current."

The listing 350 also indicates which possible "Patient Data" parameter has been selected to replace the current "Patient Data" parameter occupying the selected "Patient Data" parameter position. As depicted in layout configuration window 300, the "$V_{MAX}$" parameter 358 was selected to replace the "$V_{E\,TOT}$" parameter 344 in the seventh "Patient Data" parameter position 320G. Since "$V_{MAX}$" 358 is the new parameter in the seventh "Patient Data" parameter position 320G, the concise description 368 of the "$V_{MAX}$" parameter 358 in the listing 350 includes the word "new".

The layout configuration window 300 also includes a box for a detailed description 374 of the selected replacement "Patient Data" parameter 358 in the listing 350. As discussed above, the selected replacement "Patient Data" parameter in the exemplary layout configuration window 300 is the "$V_{MAX}$" parameter 358. Likewise, the detailed description box 374 includes a detailed description of the "$V_{MAX}$" parameter 358.

When a "Patient Data" parameter has been selected the replace the current "Patient Data" parameter occupying the selected "Patient Data" parameter position, the replacement "Patient Data" parameter is displayed as occupying the selected "Patient Data" parameter position in the preview toolbar of the layout configuration window 300. In the exemplary layout configuration window 300, the "$V_{MAX}$" parameter 326 is displayed in the preview toolbar 320 as occupying the selected seventh "Patient Data" parameter position 320G.

The layout configuration window 300 also includes an Accept button 376. When a clinician is satisfied with the layout of the "Patient Data" parameters in the preview toolbar 320, the clinician may access the Accept button 376. Once the Accept button 376 has been accessed, the "Patient Data" parameters 322-330 and 386-392 occupying the preview toolbar 320 will be reflected as the "Patient Data" parameters 340-348 and 378-384 in the underlying graphical display 700 (not depicted). The actual patient data of the new "Patient Data" parameter will then be displayed in the underlying graphical 700 (not depicted).

Figure 4:
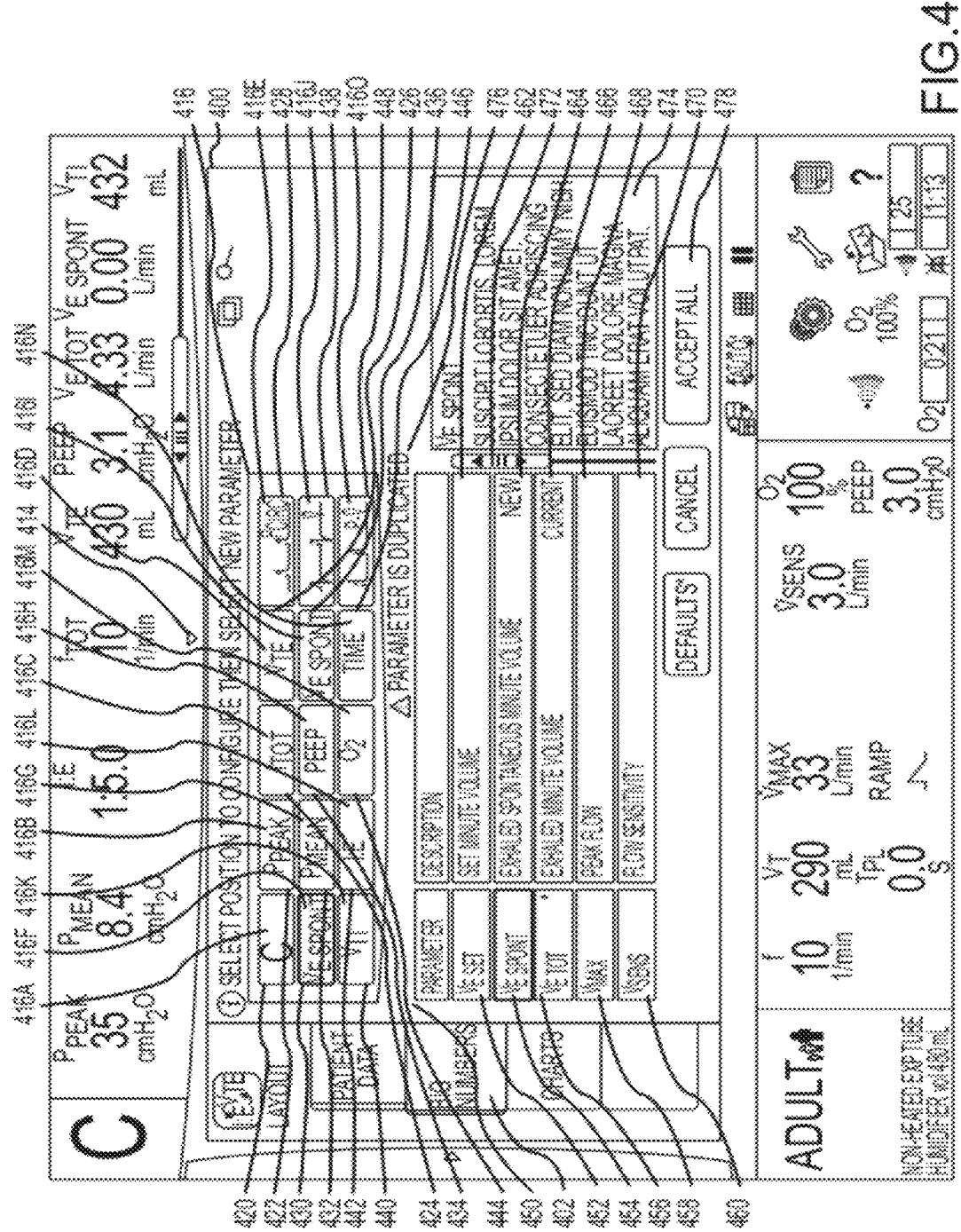
FIG. 4 is an illustration of an embodiment of a user interface for interface for configuring layout settings for a "Big Numbers" parameter.

FIG. 4 is an illustration of an embodiment of a user interface for modifying layout configuration settings for the graphical display. In FIG. 4, layout configuration window 400 depicts an embodiment in which the "Big Numbers" layout category 402 has been selected for display.

Figure 5:
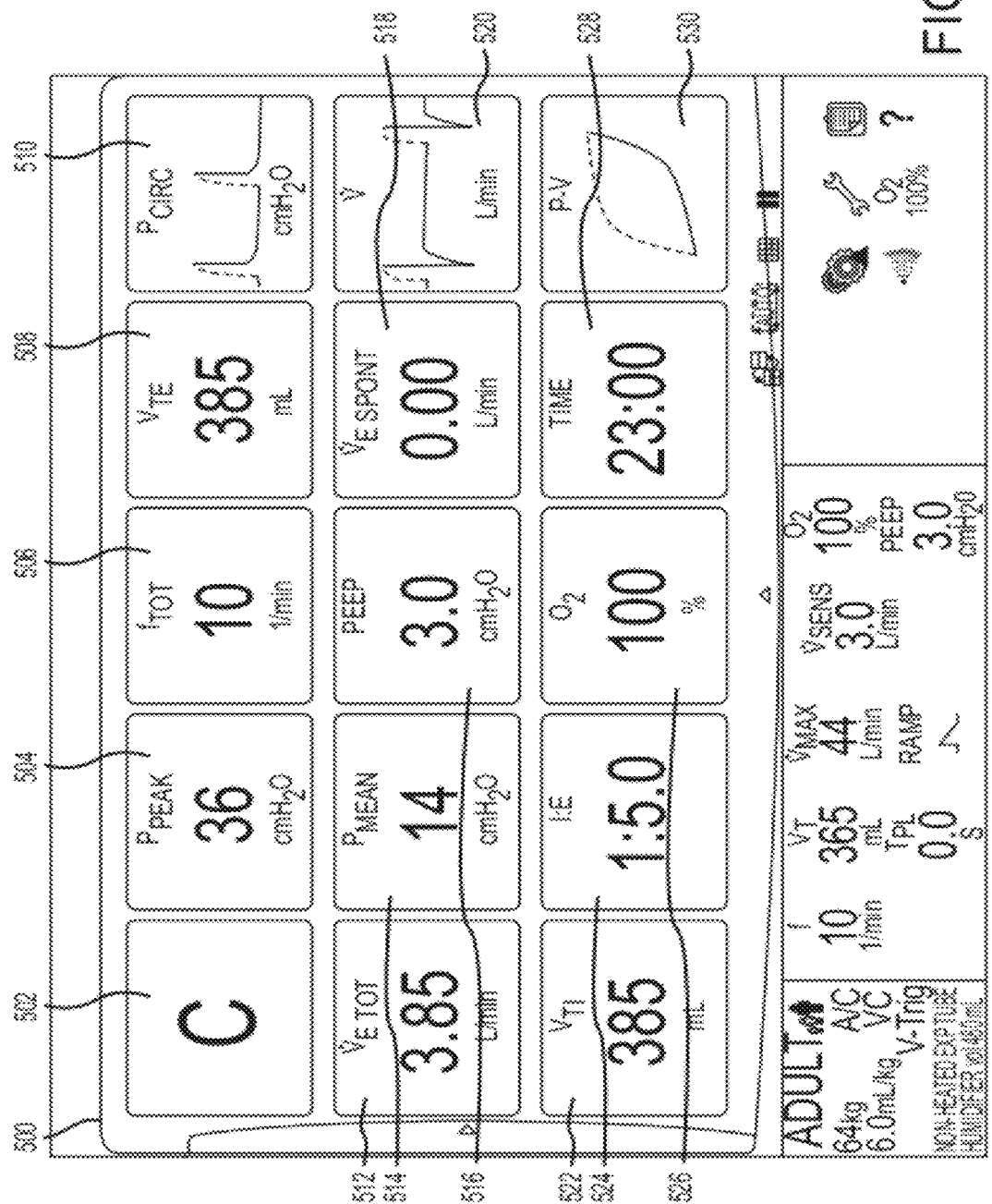
FIG. 5 is an illustration of an embodiment of a user interface displaying an expanded "Big Numbers" parameter window.

The layout configuration information in the "Big Numbers" tab 402 corresponds to the "Big Numbers" parameters "Big Numbers" window 500. In one embodiment, the "Big Numbers" window 500 is accessed by pulling down pull down arrow 414. By accessing the pull down arrow 414, the clinician can view the "Big Numbers" parameters positions in the "Big Numbers" window 500 as seen in FIG. 5. As will be described below, modifying the layout configuration settings using the "Big Numbers" tab 402 of the layout configuration window 400 changes the layout of the "Big Numbers" window 500.

Returning the FIG. 4, the "Big Numbers" tab 402 includes a preview 416 of the "Big Numbers" window 500. The preview 416 displays the available "Big Numbers" parameter positions 416A-416O and the current "Big Numbers" parameters occupying those positions 420-448. Like the "Patient Data" parameter preview toolbar 320, the preview 416 of the "Big Numbers" 500 window includes the replacement "Big Numbers" parameter. The replacement "Big Numbers" parameter will be discussed in detail below.

Underneath the preview 416 of the "Big Numbers" window 500 is a listing 450 of possible "Big Numbers" parameters 452-460, each possible "Big Numbers" parameter 452-460 accompanied by a concise description 462-470. As can be appreciated by one skilled in the art, any number of possible "Big Number" parameters can be included in the listing 450. In the exemplary layout configuration window 400, five possible "Big Numbers" parameters are displayed: "$V_{E\ SET}$" 452, "$V_{E\ SPONT}$" 454, "$V_{E\ TOT}$" 456, "$V_{MAX}$" 458, and "$V_{SENS}$" 460. Additional "Big Numbers" parameters can be displayed by accessing the scrollbar 472 to the right of the listing 450. As depicted, each possible "Big Numbers" parameter 452-460 is accompanied by a concise description 462-470. For example, the "$V_{E\ SPONT}$" parameter 454 is accompanied by a concise description of "Exhaled spontaneous minute volume" 464. In one embodiment, the listing 450 is not visible until a "Big Numbers" parameter 420-448 is selected from the preview 416.

The listing 450 also indicates which possible "Big Numbers" parameters are currently occupying a selected "Big Numbers" parameter position. For example, the "Big Numbers" parameter position 416F (directly underneath the "C") in the preview 416 of the "Big Numbers" window 500 is currently selected. The selection is indicated by a bold border. As will be appreciated by one skilled in the art, any method of indicating selection can be utilized, including but limited to, changing the background color, changing the border, changing the font, or any other method known in the art. In the exemplary layout configuration window 400, the "$V_{E\ TOT}$" parameter 456 is currently occupying the "Big Numbers" parameter position directly underneath the "C" in the preview 416. This occupation can be seen in the "Big Numbers" window 500 of the underlying graphical display as the "$V_{E\ TOT}$" parameter is currently occupying the position 512 under the "C". When a possible "Big Numbers" parameter occupies the selected "Big Numbers" parameter position, the concise description of the possible "Big Numbers" parameter includes the word "current." In the exemplary layout configuration window 400, the concise description 466 of the "$V_{E\ TOT}$" parameter 456 includes the word "current."

The listing 450 also indicates which possible "Big Numbers" parameter has been selected to replace the current "Big Numbers" parameter occupying the selected "Big Numbers" parameter position. As depicted in layout configuration window, the "$V_{SPONT}$" 454 parameter was selected to replace the "$V_{E\ TOT}$" parameter 456 in the "Big Number" parameter position 461F underneath the "C" in the preview of the "Big Numbers" window 416. Since "$V_{SPONT}$" 454 is the new parameter in the selected "Big Numbers" parameter position 416F, the concise description 464 of the "$V_{SPONT}$" parameter 454 in the listing 450 includes the word "new".

The layout configuration window 400 also includes a box 474 for a detailed description of the "Big Numbers" parameter that has been selected to replace current "Big Numbers" parameter occupying the selected "Big Numbers" parameter position. As discussed above, the selected replacement "Big Numbers" parameter in the exemplary layout configuration window 400 is the "$V_{E\ SPONT}$" parameter 454. Likewise, the detailed description box 474 includes a detailed description of the "$V_{E\ SPONT}$" parameter 454.

When a "Big Numbers" parameter has been selected the replace the current "Big Numbers" parameter occupying the selected "Big Numbers" parameter position, the replacement "Big Numbers" parameter is displayed as occupying the selected "Big Numbers" parameter position in the preview 416 in layout configuration window 400. In the exemplary layout configuration window 400, the "$Y_{E\ SPONT}$" parameter 454 is displayed in the preview 416 of the "Big Numbers" 500 window as occupying the selected "Big Numbers" parameter 416F position (below the "C") in the preview 416.

The layout configuration window 400 may also include an Accept button (not depicted). When a clinician is satisfied with the layout of the "Big Numbers" parameters in the preview 416, the clinician may access the Accept button (not depicted). Once the Accept button (not depicted) has been accessed, the "Big Numbers" parameters occupying the preview 416 of the "Big Numbers" window 500 will be reflected as the "Big Numbers" parameters in the "Big Numbers" window 500 (not depicted). The actual patient data of the new "Big Numbers" parameter will then be visible in the underlying graphical display 700 (not depicted).

As depicted in layout configuration window 400, a clinician can select a replacement "Big Number" parameter that is already present on the "Big Number" window 500. For example, the "$V_{ESPONT}$" parameter 514 is already located in the second row, fourth position from the left in the "Big Number" window 500. The clinician has also selected the "$V_{ESPONT}$" parameter 454 to occupy the "Big Number" parameter position 512 in the second row, first position from the left in the "Big Number" window 500 (not depicted). While such a replication is allowed, the clinician may be alerted that he has selected a duplicate "Big Number" parameter 476. If this is acceptable to the clinician, the clinician may access the "Accept ALL" button 478 to implement the changes the "Big Number" window 500. Like the "Accept" button (not depicted), accessing the "Accept ALL" button 478 causes the "Big Numbers" parameters in the "Big Numbers" window 500 to mirror the preview 416. The actual patient data of the new "Big Numbers" parameter will then be displayed in the underlying graphical display.

FIG. 5 depicts an expanded "Big Numbers" window 500. As discussed above, the expanded "Big Numbers" window can be displayed by accessing the pull down arrow 702 under the "Big Numbers" parameters in the upper left hand corner of the graphical display 700. The expanded "Big Numbers" window displays enlarged actual patient data for various "Big Numbers" parameters 502-530. The layout configuration of the "Big Numbers" parameters 502-528 is determined by a clinician using the layout configuration window 400.

Figure 6:
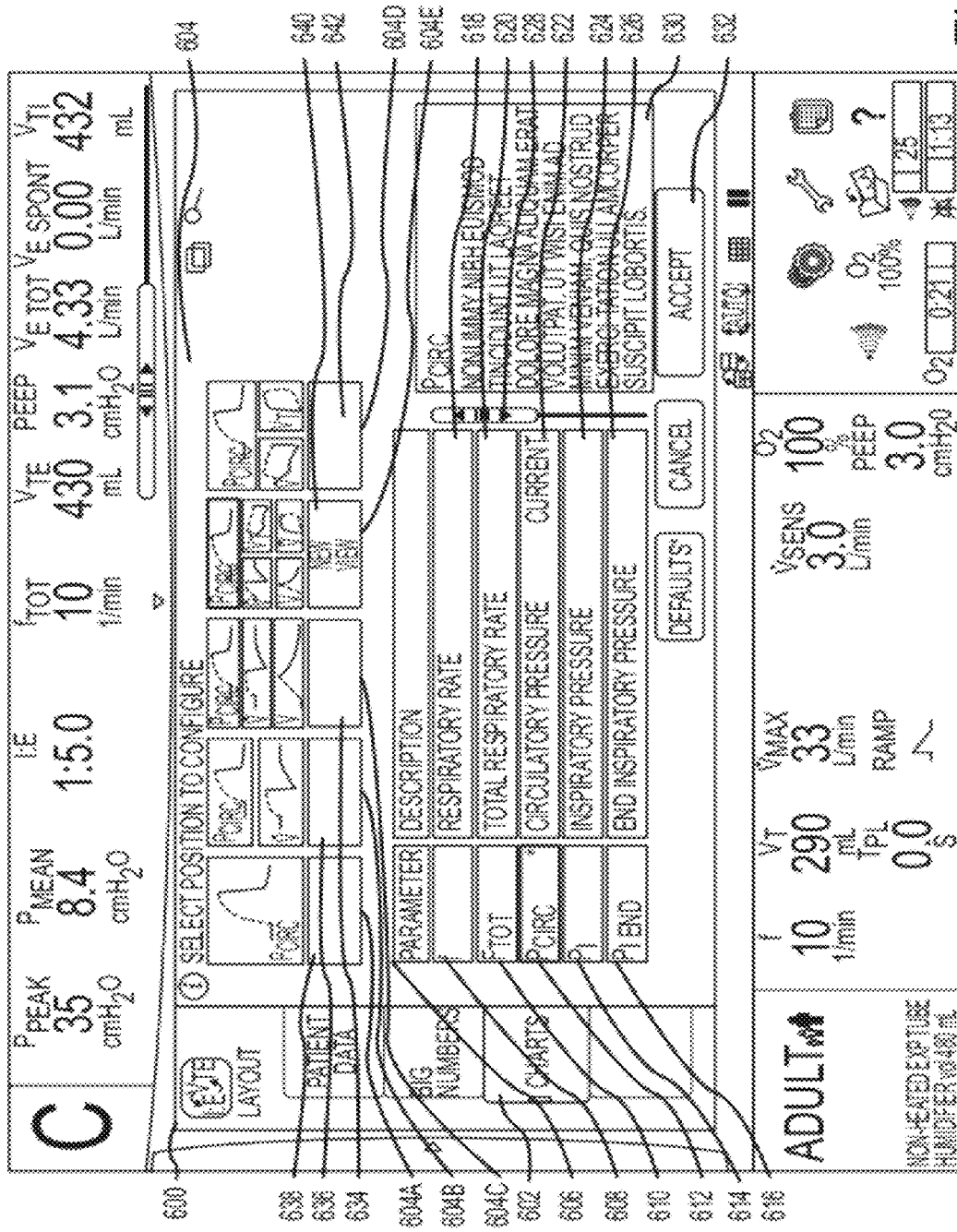
FIG. 6 is an illustration of an embodiment of a user interface for interface for configuring layout settings for a "Charts" parameter.

FIG. 6 is an illustration of an embodiment of a user interface for modifying layout configuration settings for the graphical display. In FIG. 6, layout configuration window 600 depicts an embodiment in which the "Charts" tab 602 has been selected for display.

Figure 7:
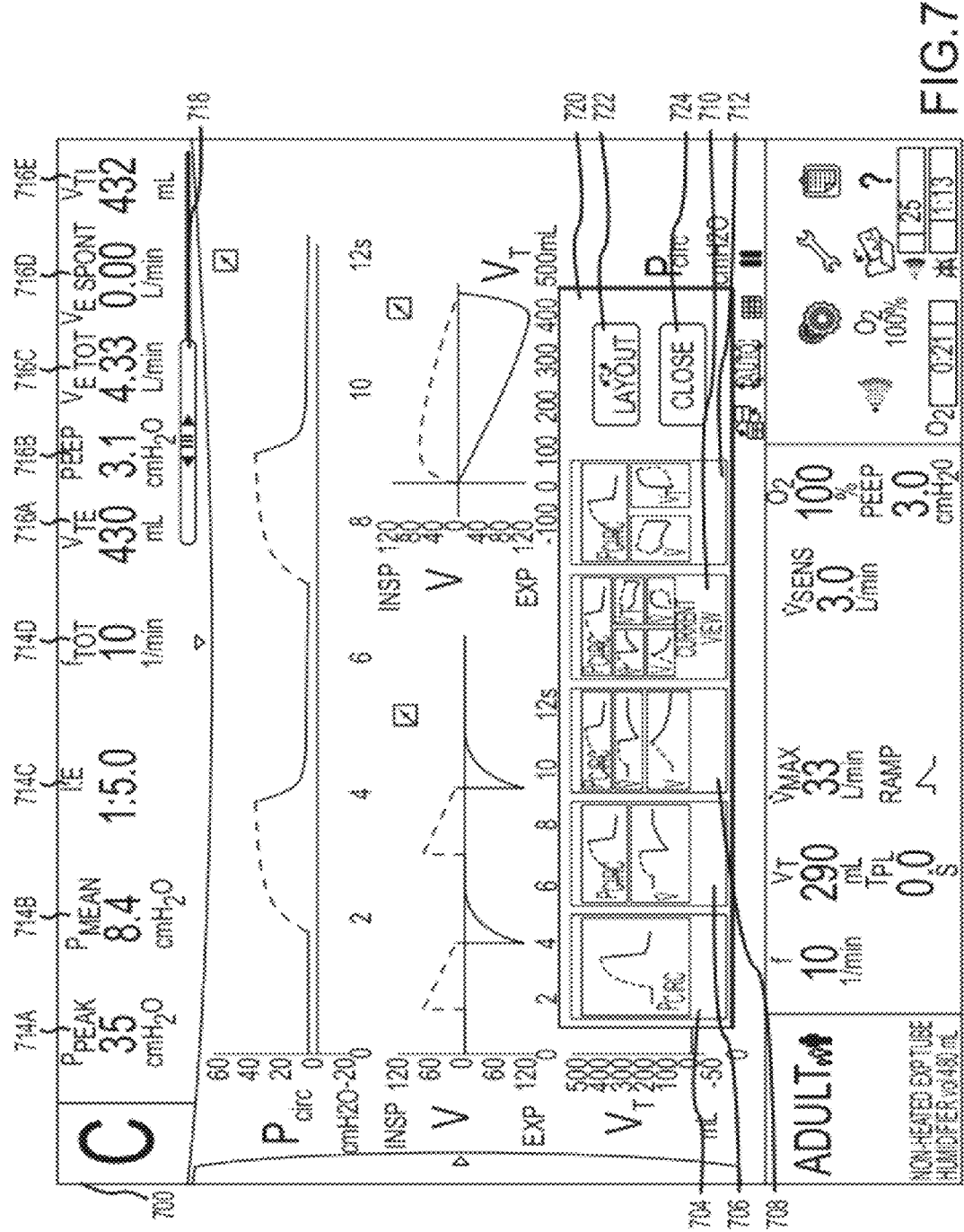
FIG. 7 is an illustration of an embodiment of a graphical display providing a selected "Charts" view.

The "Charts" tab 602 includes a preview 604 of the "Charts" views. The preview 604 corresponds to the chart configuration of the underlying graphical display 700. As can be seen in FIG. 7, the five available "Charts" views of the exemplary layout configuration window correspond to the five available views 704-712 in the underlying graphical display 700.

The preview 604 of the "Charts" views displays the available "Charts" view positions and the current "Charts" view occupying those positions. Like the "Patient Data" parameter preview toolbar and preview of the "Big Numbers" window, the preview of the "Charts" views includes the replacement "Charts" view. The replacement "Charts" view will be discussed in detail below.

The exemplary layout configuration window 600 provides five different "Charts" views 604A-604E in the preview 604. In the exemplary layout configuration window 600, the first view 604A is a single chart occupying the entire area for charts in the graphical display. The second view 604B consists of two charts, horizontally stacked on top of one another, and equally splitting the area for charts in the graphical display. The third view 604C consists of three charts, horizontally stacked on top of one another, and equally splitting the area for charts in the graphical display. The fourth view 604D consists of five charts. One chart is larger than the others and is arranged horizontally on top of the other charts. The other four charts split the remaining area for charts below the larger chart in the graphical display. The four charts are arranged in rows of two and one row is stacked on top of the other row. The fifth view 604E consists of three charts. One chart is larger than the others and is arranged horizontally on top of the other charts. The other two charts split the remaining area for charts below the larger chart in the graphical display. The two charts are arranged in a row next to one another. As will be appreciated by one of skill in the art, any number of "Charts" views can be displayed. Furthermore, the number and arrangement of charts in each individual view can also vary.

Underneath the preview 604 of the "Charts" view is a listing 606 of possible "Charts" view parameters 608-616, each possible "Charts" view parameter accompanied by a concise description 618-626. As can be appreciated by one skilled in the art, any number of possible "Charts" view parameters can be included in the listing 606. In the exemplary layout configuration window 600, five possible "Charts" parameters are displayed: "f" 608, "$f_{TOT}$" 610, "$P_{CIRC}$" 612, "$P_I$" 614, and "$P_{I\,END}$" 616. Additional "Charts" view parameters can be displayed by accessing the scrollbar 628 to the right of the listing 606. As depicted, each possible "Charts" view parameter is accompanied by a concise description. For example, the "$P_{CIRC}$" parameter 612 is accompanied by a concise description of "Circulatory pressure" 622

The listing 606 also indicates which possible "Charts" view parameters are currently occupying a selected "Charts" view parameter position. For example, the largest "Charts" view parameter position in the fourth "Charts" view 604D from the left is currently selected. The selection is indicated by a bold border. As will be appreciated by one skilled in the art, any method of indicating selection can be utilized, including but limited to, changing the background color, changing the border, changing the font, or any other method known in the art. In the exemplary layout configuration window 600, the "$P_{CIRC}$" parameter 612 is currently occupying the largest "Charts" view position in the fourth "Charts" view 604D from the left. This occupation can be seen in the exemplary graphical display 700. When a possible "Charts" view parameter occupies the selected "Charts" view parameter position, the concise description of the possible "Charts" view parameter includes the word "current." As depicted, the "$P_{CIRC}$" parameter 612 includes the word "current" in its concise description 622.

The layout configuration window 600 also includes a box 630 for a detailed description of the "Charts" view parameter selected in the listing. In the exemplary layout configuration window 600, the "Charts" view parameter selected in the listing 606 is the same parameter as is currently occupying the selected "Charts" view parameter position in the preview 604.

As the "$P_{CIRC}$" parameter 612 is selected in the listing, the detailed description box 630 includes a detailed description of the "$P_{CIRC}$" parameter 612.

As with the "Patient Data" tab and the "Big Numbers" tab, the currently selected "Charts" view parameter in the preview 604 can be replaced with a new "Charts" view parameter. When a "Charts" view parameter has been selected from the listing 606 to replace the current "Charts" view parameter occupying the selected "Charts" view parameter position, the replacement "Charts" view parameter is displayed as occupying the selected "Charts" view parameter position in the preview 604 and the button 640 below displays the words "new view."

A clinician may change the "Charts" view parameters associated with any of the "Charts" views. A clinician may access any of the buttons 634-642 to select the above "Charts" view 604A-604E. Once a "Charts" view has been selected, the "Charts" view will indicate selection and the associated button 634-642 below the selected "Charts" view will display the words "current view." (not depicted). As will be appreciated by one skilled in the art, any method of indicating selection can be utilized, including but limited to, changing the background color, changing the border, changing the font, or any other method known in the art.

The layout configuration window 600 also includes an Accept button 632. When a clinician is satisfied with the layout of the "Charts" view parameters in the preview 604, the clinician accesses the Accept button 632. Once the Accept button 632 has been accessed, the "Charts" view parameters occupying the preview 604 will be reflected as the "Charts" parameters in the underlying graphical display 700. The actual patient data corresponding to the new "Charts" view parameter will then be displayed in the underlying graphical display.

As will be appreciated by one skilled in the art, graphical representations of some parameters will lend themselves more easily to certain chart view parameter positions than other parameters. For example, one "Chart" views parameter may not be visually pleasing if represented in the elongated, top "Charts" view parameter position of the selected fourth "Charts" view 604D from the left. In one embodiment, the GUI may display a warning to a clinician before the clinician implements certain "Charts" view parameters in certain "Charts" view parameter positions. In another embodiment, the clinician may be blocked from selecting certain parameters for certain "Charts" view parameter positions.

FIG. 7 represents an exemplary underlying graphical display 700 presented to the clinician when the "switch" button 302 has been accessed. As discussed above, the "Big Numbers" parameters 714 are located to the upper left of the display while the "Patient Data" parameters 716 are located in the upper right. Furthermore, additional "Big Numbers" parameters can be viewed by accessing the pull down arrow 702. Additional "Patient Data" parameters can be viewed by accessing the scrollbar 718. As will be appreciated by one skilled in the art, the "Big Numbers" parameters and "Patient Data" parameters are not limited to the upper left and upper right corners of the screen, respectively. Rather, any number of "Patient Data" and "Big Numbers" parameters can be configured for display anywhere on the screen. Moreover, new tabs on the layout configuration window can be created to enable display of new parameters.

The layout configuration interface can provide underlying graphical display 700. The exemplary graphical display 700 depicts the same "Charts" view 710 as selected in exemplary layout configuration window 600. Like the preview 604 in the layout configuration window 600, the selected charts view 604D has one large chart with four charts, arranged in rows of two, located below it.

The layout configuration interface can also provide a "Quick Charts" view menu 720. The "Quick Charts" view menu 720 displays the currently configured "Charts" views 704-712. In the exemplary "Charts" view menu 720, five configured "Charts" views are displayed. The current "Chart" view 710 in the graphical display is indicated by the words "current view" in the "Charts" view menu 720. As will be appreciated, any combination of colors, words, symbols, etc. can be used to indicate the current view.

As will be appreciated, a clinician can change the current "Charts" view of the graphical display 700 by accessing a different "Charts" view in the "Charts" view menu. A new "Charts" view can be displayed by accessing one of the other four configured "Charts" views (i.e. 704-708 or 712) in the "Chart" view menu 720. If another configured "Charts" view is selected, the underlying graphical display is immediately changed to reflect the newly selected "Charts" view and the "Quick Charts" view menu 720 is automatically closed. By using the "Quick Charts" view menu 720, a clinician can select a currently configured "Charts" view 704-710 but cannot change the parameters included in the positions of any "Charts" view 704-710 layouts. In order to change the parameters in the "Charts" view 704-710 layouts, a clinician must access the Charts tab 602 of layout configuration window 600.

The "Quick Charts" view menu 720 also includes a "Layout" button 722. The "Layout" button 722 allows a clinician to switch between the "Quick Charts" view menu 720 and the layout configuration windows 300, 500, and 600. The "Charts" view menu also includes a "Close" button 724. The "Close" button 724 allows a clinician to close the "Charts" view menu 720.

As will be appreciated, a clinician cannot change the configuration of available "Charts" views 704-712, "Big Number" parameters 714 in the un-expanded "Big Number" toolbar, "Big Number" parameters 502-530 in the expanded "Big Number" window, or "Patient Data" parameters 716 from the underlying graphical display 700 The displayed views and parameters are preconfigured. In order to change the configuration of the available "Charts" views 704-712, "Big Number" parameters 714 in the un-expanded "Big Number" toolbar, "Big Number" parameters 502-530 in the expanded "Big Number" window, or "Patient Data" parameters 716, the clinician must first access the "Layout" button 722 and then change the views and or parameters using the layout configuration window 300, 500, and 600 as discussed above.

It will be clear that the systems and methods described herein are well adapted to attain the ends and advantages mentioned as well as those inherent therein. Those skilled in the art will recognize that the methods and systems within this specification may be implemented in many manners and as such is not to be limited by the foregoing exemplified embodiments and examples. In other words, functional elements being performed by a single or multiple components, in various combinations of hardware and software, and individual functions can be distributed among software applications at either the client or server level. In this regard, any number of the features of the different embodiments described herein may be combined into one single embodiment and alternative embodiments having fewer than or more than all of the features herein described are possible.

While various embodiments have been described for purposes of this disclosure, various changes and modifications may be made which are well within the scope of the present invention. Numerous other changes may be made which will readily suggest themselves to those skilled in the art and which are encompassed in the spirit of the disclosure and as defined in the appended claims.

What is claimed is:

1. A user interface for providing layout configuration for a graphical display associated with a ventilator, the ventilator configured with a computer, the computer comprising a processor and a memory, the memory storing computer executable instructions that, when executed, provide a user interface including a graphical user interface for accepting commands and for displaying information, the user interface comprising:
   at least one window associated with the user interface; and
   elements within the at least one window comprising:
      a first set of selection elements for selecting a layout category;
      a second set of selection elements, each of the second set of selection elements indicating a parameter position within a layout associated with a selected one the first set of selections elements and a first parameter currently associated with the parameter position; and
      a third set of selection elements for indicating a replacement parameter for the parameter position, wherein selection of the replacement parameter replaces the first parameter with the selected replacement parameter.

2. The user interface of claim 1, wherein each layout category corresponds to a set of data on the graphical display of the graphical user interface.

3. The user interface of claim 1, wherein the first set of selection elements comprise at least one of:
   a tab for selecting a patient data layout category;
   a tab for selecting a big numbers layout category; and
   a tab for selecting a charts layout category.

4. The user interface of claim 1, wherein the second set of selection elements includes a preview of the set of data on the graphical display, the preview comprising a currently displayed parameter for each parameter position.

5. The user interface of claim 4, wherein the third set of selection elements comprises a listing of possible parameters for selection as the replacement parameter.

6. The user interface of claim 5, wherein selection of one of the possible parameters in the third set of selection elements causes the selected possible parameter to occupy the indicated parameter position in the preview.

7. The user interface of claim 6, wherein the one or more elements further comprises a fourth set of selection elements, wherein one element of the fourth set of selection element comprises a button for implementing the replacement parameter in the graphical display.

8. The user interface of claim 7, wherein when the button is selected actual patient data associated with the replacement parameter is visible in the graphical display.

9. A computer-readable storage medium having instructions that when executed provide a user interface for providing layout configuration for a graphical display associated with a ventilator, the user interface comprising:
   at least one window associated with the user interface; and
   elements within the at least one window comprising:
      a first set of selection elements for selecting a layout category;
      a second set of selection elements, each of the second set of selection elements indicating a parameter position within a layout associated with a selected one the first set of selections elements and a first parameter currently associated with the parameter position; and a third set of selection elements for indicating a replacement parameter for a selected parameter position, wherein selection of the replacement parameter replaces the first parameter in the parameter position.

10. The computer-readable storage medium of claim 9, wherein each layout category corresponds to a set of data on the graphical display of the graphical user interface.

11. The computer-readable storage medium of claim 9, wherein the first set of selection elements comprise at least one of:
 a tab for selecting a patient data layout category;
 a tab for selecting a big numbers layout category; and
 a tab for selecting a charts layout category.

12. The computer-readable storage medium of claim 9, wherein the second set of selection elements includes a preview of the set of data on the graphical display, the preview comprising a currently displayed parameter for each parameter position.

13. The computer-readable storage medium of claim 12, wherein the third set of selection elements comprises a listing of possible parameters for selection as the replacement parameter.

14. The computer-readable storage medium of claim 13, wherein selection of one of the possible parameters in the third set of selection elements causes the selected possible parameter to occupy the indicated parameter position in the preview.

15. The computer-readable storage medium of claim 14, wherein the one or more elements further comprises a fourth set of selection elements, wherein one element of the fourth set of selection element comprises a button for implementing the replacement parameter in the graphical display.

16. The computer-readable storage medium of claim 15, wherein when the button is selected actual patient data associated with the replacement parameter is visible in the graphical display.

17. A ventilatory system configured with a computer, the computer comprising a processor and a memory, the memory storing computer executable instructions that, when executed, provide a user interface for providing layout configuration for a graphical display associated with a ventilator, comprising:
 at least one window associated with the user interface; and
 elements within the at least one window comprising:
  a first set of selection elements for selecting a layout category;
  a second set of selection elements, each of the second set of selection elements indicating a parameter position within a layout associated with a selected one the first set of selections elements and a first parameter currently associated with the parameter position; and
  a third set of selection elements for indicating a replacement parameter for the parameter position, wherein the replacement parameter replaces the first parameter.

18. The ventilatory system of claim 17, wherein each layout category corresponds to a set of data on the graphical display of the graphical user interface.

19. The ventilatory system of claim 17, wherein the first set of selection elements comprise at least one of:
 a tab for selecting a patient data layout category;
 a tab for selecting a big numbers layout category; and
 a tab for selecting a charts layout category.

20. The ventilatory system of claim 17, wherein the second set of selection elements includes a preview of the set of data on the graphical display, the preview comprising a currently displayed parameter for each parameter position.

* * * * *

UNITED STATES PATENT AND TRADEMARK OFFICE
CERTIFICATE OF CORRECTION

PATENT NO. : 8,499,252 B2  
APPLICATION NO. : 12/844579  
DATED : July 30, 2013  
INVENTOR(S) : John Skidmore Page 1 of 1

It is certified that error appears in the above-identified patent and that said Letters Patent is hereby corrected as shown below:

Title Page, add Item (60),  
-- Related U.S. Application Data, Provisional Application No. 61/287,914, filed on December 18, 2009 --

Signed and Sealed this  
Twenty-sixth Day of November, 2013

Margaret A. Focarino  
*Commissioner for Patents of the United States Patent and Trademark Office*